(12) United States Patent
Sudo et al.

(10) Patent No.: US 7,091,238 B1
(45) Date of Patent: Aug. 15, 2006

(54) THIENYLHYDRAZON WITH DIGITALIS-LIKE PROPERTIES (POSITIVE INOTROPIC EFFECTS)

(75) Inventors: Roberto Takashi Sudo, Rio de Janeiro (BR); Edson X. Albuquerque, Baltimore, MD (US); Eliezer J. De Barreiro, Rio de Janeiro (BR); Yasco Aracava, Rio de Janeiro (BR); Wagner Monteiro Cintra, Rio de Janeiro (BR); Paulo De Assis Melo, Niteroi (BR); Francois Germain Noel, Rio de Janeiro (BR); Gisele Zapata Sudo, Rio de Janeiro (BR); Claudia Lucia Martins Da Silva, Rio de Janeiro (BR); Newton Goncalves de Castro, Rio de Janeiro (BR); Patricia Dias Fernandes, Rio de Janeiro (BR); Carlos Alberto Manssour Fraga, Rio de Janeiro (BR); Ana Luisa Palhares De Miranda, Petropolis (BR)

(73) Assignee: University of Maryland, Baltimore, MD (US)

( * ) Notice: Subject to any disclaimer, the term of this patent is extended or adjusted under 35 U.S.C. 154(b) by 109 days.

(21) Appl. No.: 10/070,328

(22) PCT Filed: Jun. 21, 2000

(86) PCT No.: PCT/US00/17024

§ 371 (c)(1),
(2), (4) Date: Apr. 8, 2004

(87) PCT Pub. No.: WO00/78754

PCT Pub. Date: Dec. 28, 2000

Related U.S. Application Data

(60) Provisional application No. 60/140,352, filed on Jun. 21, 1999.

(51) Int. Cl.
*C07D 409/12* (2006.01)
*A61K 31/381* (2006.01)
*C07D 317/62* (2006.01)

(52) U.S. Cl. ......................... 514/444; 549/60
(58) Field of Classification Search .................. 549/60; 514/444
See application file for complete search history.

(56) References Cited

FOREIGN PATENT DOCUMENTS

EP   0 079 050   5/1983
EP   0 219 112   4/1987

OTHER PUBLICATIONS

Van Heeswijk, PubMed Abstract (Ther Drug Monit. 24(3):323-31) Jun. 2002.*
Marcus et al., PubMed Abstract (Intervirology 45(4-6): 260-6), 2002.*
Simone, Cecil Textbook of Medicine, 20$^{th}$ Edition, vol. 1, pp. 1004-1010, 1996.*
Singh et al., Immune therapy in inflammatory bowel Disease and models of colitis, British Journal of Surgery, 88:1558-1569, 2001.*
Robinson, Medical Therapy of Inflammatory Bowel Diseases for the 21$^{st}$ Century, Eur. J. Surg. Suppl. 582:90-98, 1998.*
Bremmer et al., Therapy of Crohn's disease in childhood, Expert Opin. Pharmaceuticals. 3(7): 809-825, 2002.*
Beers et al., Crohn's Disease & Ulcerative Colitis, The Merck Manual of Diagnosis and Therapy, Seventeenth Edition, Section 3, Chapter 31, 1999.*
Koren, Diastolic Congestive Heart Failure, Jacksonville Medicine, Feb. 2002.*
Lerman, Endothelial Dysfunction and Ischemia, Oct. 2002.*
Silverman, The Organic Chemistry of Drug Design and Drug Action, pp. 352-400 (1992).*
Bundgaard, Design of Prodrugs, p. 1, 1985.*
Kucukguzel, et al. "Synthesis and antimycobacterial activity of some coupling products from 4-aminobenzoic acid hydrazones" European Journal of Medicine, Chem. Chim. Ther., (Dec. 1999) vol. 34, No. 12 pp. 1093-1100.
Mazzone et al. 2-Pyridyl-5-alkoxyphenyl—1, 3,4-thiadiazo les by the action of sulfur on methylpyridines in the presence of alkoxyhydrazines, J Heterocyclic Chem. (1984) vol. 21 pp. 181-184.
Mazzonw et al., Su alcuni aroilidrazoni di alogenobenzaldeidi e 2,5-diaril-1, 3, 4-ossdiazoli alogeno-sostituiti II Farmaco, (1978) vol. 33, pp. 963-966.
Tihany et al. "Pyrazolecarboxylic acid hydrazides as antiinflammatory agents. New selective lipoxygenase inhibitors" European Journal of Medicine -Chem. Chim. Ther., (1984) vol. 19, No. 5 pp. 433-439.

* cited by examiner

*Primary Examiner*—Deepak Rao
(74) *Attorney, Agent, or Firm*—Venable LLP; Thomas G. Wiseman

(57) ABSTRACT

The invention discloses a compound having the formula (I) wherein $R_1$ is selected from the group consisting of hydrogen, alkyl of 1 to 6 carbon atoms, unsubstituted phenyl, and substituted phenyl; $R_2$ is selected from the group consisting of H, alkene, un-substituted phenol, and substituted phenyl; and pharmaceutically acceptable salts thereof, having digitalis-like properties. The invention further discloses a novel method to synthesize 3,4-methylenedioxybenzoyl-2-thienylhydrazone (LASSBio-294). LASSBio-294 produces positive inotropic effect on cardiac and skeletal muscle. The invention is useful for the treatment of congestive heart failure and muscle fatigue. It lacks toxic effects seen in digitalis glycosides.

21 Claims, 40 Drawing Sheets

| ORGAN/TISSUE | CONTROL (SALINE) | SOLVENT (DMSO/PG) | LSSBio-294 2 mg/kg | LSSBio-294 10 mg/kg |
|---|---|---|---|---|
| BRAIN | NS* | NS | NS | NS |
| SKELETAL MUSCLE | NS | NS | NS | NS |
| HEART | NS | NS | NS | NS |
| THYMUS | NS | NS | NS | NS |
| LUNG | NS | NS | NS | NS |
| LIVER | NS** | NS | NS | NS |
| SPLEEN | NS | NS | NS | NS |
| DUODENUM | NS | NS | NS | NS |
| PANCREAS | NS | NS | NS | NS |
| KIDNEY | NS | NS | NS | NS |
| SUPRARENAL | NS | NS | NS | NS |
| URINARY BLADDER | NS | NS | NS | NS |

* NS INDICATES NO SIGNIFICANT CHANGE WHEN COMPARED TO A CONTROL UNINJECTED ANIMAL.
** ONE ANIMAL OF THE CONTROL (SALINE) GROUP SHOWED AN INFLAMMATORY PROCESS (MONONUCLEAR INFILTRATION) IN THE LIVER.

FIG. 1A

| DAY | SALINE | | | | | | SOLVENT | | | | | | LASSBio-294 | | | | | | LASSBio-294 | | | | | |
|---|---|---|---|---|---|---|---|---|---|---|---|---|---|---|---|---|---|---|---|---|---|---|---|---|
| | 1 | 2 | 3 | 4 | 5 | 6 | 1 | 2 | 3 | 4 | 5 | 6 | 1 | 2 | 3 | 4 | 5 | 6 | 1 | 2 | 3 | 4 | 5 | 6 |
| 1 | 18 | 16.4 | 19.4 | 17.4 | 17.7 | 18.4 | 18.6 | 19.8 | 17.2 | 17.7 | 16.2 | 18.9 | M | M | M | 15.8 | 16.5 | 15.7 | 15.6 | 15 | 15 | 16.3 | 15.7 | 15 |
| 2 | 18.6 | 16.4 | 18.3 | 17.3 | 17.6 | 18.8 | 17.6 | 18.6 | 16 | 17.7 | 14.7 | 18.2 | 18.8 | 17.2 | 16 | D | 15.2 | 14.6 | 15.8 | 14.7 | 14.9 | 16.7 | 15.7 | 15.7 |
| 3 | 18.5 | 16.3 | 18.4 | 17.6 | 18.6 | 19.4 | 18.2 | 18.8 | 16.6 | 17.8 | 14.2 | 19 | 18.3 | 18.2 | 16.3 | | 15 | 14.4 | 16.5 | 15 | 15 | 17.9 | 16.7 | 17 |
| 4 | 19.3 | 16.6 | 18.4 | 17.7 | 18.3 | 20.1 | 18.3 | 18.3 | 16.6 | 17.3 | 14.2 | 18.4 | 19 | 16.8 | 16.6 | | 15 | 14.6 | 16.6 | 14.8 | 15.4 | 18 | 17.4 | 16.5 |
| 5 | 19.9 | 16.8 | 18.2 | 17.9 | 19 | 20.5 | 18.8 | 17.4 | 17.5 | 16.9 | 13.6 | 18.7 | 20 | 17 | 17.2 | | 15.5 | 14.7 | 16.9 | 15.7 | 15.8 | 18.4 | 18 | 17.1 |
| 6 | 21 | 17.8 | 18 | 18.5 | 20 | 22.5 | 20.4 | 16.6 | 17.5 | 16.7 | D | 18.7 | 21.8 | 19 | 19.1 | | 18.1 | 15.4 | 17.5 | 16.6 | 15.8 | 19.6 | 20 | 17.9 |
| 7 | 21.5 | 18 | 18 | 18.8 | 20 | 23 | 21 | 17.2 | 19 | 16 | | 20.2 | 22 | 20 | 19.5 | | 18.5 | 16 | 18 | 17 | 16 | 20 | 20 | 18.1 |
| 8 | 20 | 17 | 18 | 18 | 19.7 | 22.5 | 19 | 17.7 | 20 | 16.5 | | 20.5 | 22 | 17.9 | 18 | | 16.9 | 14.5 | 17 | 15.5 | 14.8 | 18.7 | 20 | 17 |
| 9 | 19.2 | 20 | 18.4 | 18.4 | 20 | 22.9 | 20.4 | 18.8 | 18.7 | 14.6 | | | 21.3 | 21.2 | 17.6 | | 17 | 14.4 | 17 | 15.5 | 15 | 18.2 | 18 | 16.6 |
| 10 | 20.8 | 19 | 18.5 | 19 | 19.5 | 22 | 21 | 18 | 18.5 | D | | 20.5 | 21 | 15.8 | 17.5 | | 16.5 | 15 | 19.5 | 18 | 15.3 | 18.5 | 19.1 | 17 |
| 11 | 21.5 | 19 | 19 | 18 | 19 | 22.5 | 21.9 | 19 | 18.7 | | | 21 | 19.8 | 16 | 18 | | 17 | 16 | 20 | 19 | 17 | 19 | 19.5 | 18 |
| 12 | 20.5 | 17.5 | 17.5 | 18.5 | 20.5 | 23.3 | 21.3 | 19.7 | 20.1 | | | 22.4 | 24.1 | 19.7 | 18.9 | | 17.5 | 15.3 | 17.7 | 15.9 | 15.5 | 20.2 | 20.1 | 18.5 |
| 13 | 20.4 | 17.2 | 17.2 | 18.2 | 20.9 | 22.9 | 22.1 | 19.7 | 21.2 | | | 23.2 | 24.5 | 21.3 | 18.6 | | 17.7 | 15.6 | 17.3 | 15.9 | 15 | 23.3 | 19.7 | 18.6 |
| 14 | 20.9 | 17.8 | 17.8 | 18.2 | 21 | 23.2 | 22.2 | 19 | 21 | | | 23.4 | 25.5 | 21.5 | 19 | | 18.8 | 16.8 | 17.8 | 16.4 | 15.1 | 19.1 | 20.6 | 18.7 |
| 15 | 20.6 | 17.4 | 17.4 | 18.2 | 20.8 | 23.3 | 22.3 | 18.8 | 21.5 | | | 23.1 | 26.3 | 21.9 | 18.9 | | 19.4 | 16.2 | 18.7 | 16.5 | 15 | 19.9 | 20 | 18.6 |

FIG. 1B

|  | MOUSE # | HEMATOCRIT (%) | MEAN | S.D. | Lecx10³/m | m3 | MEAN | S.D. | HEM. | /mm3 | MEAN | S.D. |
|---|---|---|---|---|---|---|---|---|---|---|---|---|
| SALINE | 1 |  | 44.5 | 0.71 |  |  | 4.93 | 3.15 |  |  | 9.77 | 3.41 |
|  | 2 | 44 |  |  | 143 | 7.15 |  |  | 981 | 7.36 |  |  |
|  | 3 | 41 |  |  | 275 | 13.75 |  |  | 681 | 10.2 |  |  |
|  | 4 | 48 |  |  | 47 | 2.35 |  |  | 453 | 13.6 |  |  |
|  | 5 | 47 |  |  | 20 | 1 |  |  | 417 | 12.51 |  |  |
|  | 6 | 45 |  |  | 54 | 2.7 |  |  | 406 | 12.18 |  |  |
| SOLVENT | 1 | 43 | 44.0 | 1.14 | 54 | 2.7 | 3.76 | 1.43 | 333 | 5.99 | 10.33 | 2.92 |
|  | 2 |  |  |  |  |  |  |  |  |  |  |  |
|  | 3 | 43 |  |  | 117 | 5.85 |  |  | 376 | 11.28 |  |  |
|  | 4 |  |  |  |  |  |  |  |  |  |  |  |
|  | 5 | 46 |  |  | 69 | 3.45 |  |  | 406 | 12.18 |  |  |
|  | 6 | 44 |  |  | 61 | 3.05 |  |  | 396 | 11.88 |  |  |
| LASSBio-294 2 mg/kg | 1 | 47 | 46.2 | 1.30 | 89 | 4.45 | 3.76 | 1.04 | 418 | 12.54 | 12.38 | 0.83 |
|  | 2 | 44 |  |  | 67 | 3.35 |  |  | 399 | 11.97 |  |  |
|  | 3 | 47 |  |  | 44 | 2.2 |  |  | 398 | 11.94 |  |  |
|  | 4 |  |  |  |  |  |  |  |  |  |  |  |
|  | 5 | 46 |  |  | 79 | 3.95 |  |  | 459 | 13.77 |  |  |
|  | 6 | 47 |  |  | 97 | 4.85 |  |  | 390 | 11.7 |  |  |
| LASSBio-294 10 mg/kg | 1 | 49 | 48.5 | 0.71 | 40 | 2 | 2.80 | 1.13 | 385 | 11.55 | 10.50 | 1.48 |
|  | 2 | 48 |  |  | 56 | 2.8 |  |  | 200 | 6 |  |  |
|  | 3 | 45 |  |  | 164 | 8.2 |  |  | 350 | 10.5 |  |  |
|  | 4 | 48 |  |  | 64 | 3.2 |  |  | 305 | 9.15 |  |  |
|  | 5 | 47 |  |  | 98 | 4.9 |  |  | 535 | 16.05 |  |  |
|  | 6 | 48 |  |  | 72 | 3.6 |  |  | 315 | 9.45 |  |  |

FIG. 1C

| | GLUCOSE mg/dl | UREA mg/dl | CREATINE mg/dl | TOTAL PROTEIN g/dl | ALBUMIN g/dl | GLOBULINS g/dl | RATIO A/G | TGO U/l | TGP U/l |
|---|---|---|---|---|---|---|---|---|---|
| SALINE | 182 | 57 | 0.4 | 6.1 | 3.8 | 2.3 | 1.6 | 148 | 80 |
| | 30 | 41 | 0.5 | 6.0 | 3.6 | 2.4 | 1.5 | 194 | 68 |
| | 45 | 51 | 0.5 | 5.6 | - | - | - | 233 | 62 |
| | 29 | 35 | 0.2 | 5.5 | - | - | - | 130 | - |
| | 170 | 56 | 0.5 | 5.3 | 3.6 | 1.7 | 2.1 | 164 | 65 |
| SOLVENT | 155 | 58 | 0.3 | 5.0 | 3.3 | 1.7 | 1.9 | 117 | 79 |
| | 105 | 61 | 0.3 | 4.8 | 2.8 | 2.0 | 1.4 | 152 | 69 |
| | 122 | 53 | 0.6 | 4.9 | 3.3 | 1.6 | 2.1 | 136 | 54 |
| | 124 | 55 | 0.3 | 5.3 | 3.4 | 1.9 | 1.7 | 154 | 63 |
| LASSBio-294 2 mg/kg | 97 | 55 | 0.5 | 4.8 | 3.1 | 1.7 | 1.8 | 106 | 56 |
| | 131 | 34 | 0.4 | 4.9 | 3.2 | 1.7 | 1.8 | 124 | 45 |
| | 175 | 77 | 0.2 | 6.0 | - | - | - | 101 | - |
| | 166 | 63 | 0.4 | 5.6 | 3.7 | 1.9 | 1.9 | 211 | 100 |
| | 93 | 65 | 0.4 | 6.0 | - | - | - | 198 | 84 |
| LASSBio-294 10 mg/kg | 179 | 45 | 0.4 | - | - | - | - | 259 | 92 |
| | 70 | 55 | 0.3 | 4.9 | 3.8 | 1.1 | 3.4 | 148 | 74 |
| | 86 | 91 | 0.6 | - | - | - | - | 137 | 50 |
| | 132 | 67 | 0.6 | 6.1 | - | - | - | 284 | 127 |
| | 134 | 72 | 0.5 | 7.7 | - | - | - | 100 | 64 |
| | 120 | 44 | 0.3 | 5.5 | 3.8 | 1.7 | 2.2 | 156 | 111 |

FIG. 1D

| DMSO | $T_P$(ms) | $T_{0.5}$(ms) | $T_{0.8}$(ms) |
|---|---|---|---|
| 1 | 36 | 38 | 60 |
| 2 | 31 | 33 | 52 |
| 3 | 41 | 34 | 53 |
| AVERAGE | 36 | 35 | 55 |
| SE | 2.89 | 1.53 | 2.52 |
|  |  |  |  |
| #294 (25uM) | $T_P$(ms) | $T_{0.5}$(ms) | $T_{0.8}$(ms) |
| 1 | 42 | 38 | 58 |
| 2 | 41 | 30 | 48 |
| 3 | 41 | 31 | 49 |
| AVERAGE | 41 | 33 | 52 |
| SE | 0.33 | 2.52 | 3.18 |
|  |  |  |  |
| AVERAGE (#294/DMSO) | 1.14 | 0.94 | 0.95 |

FIG. 1E

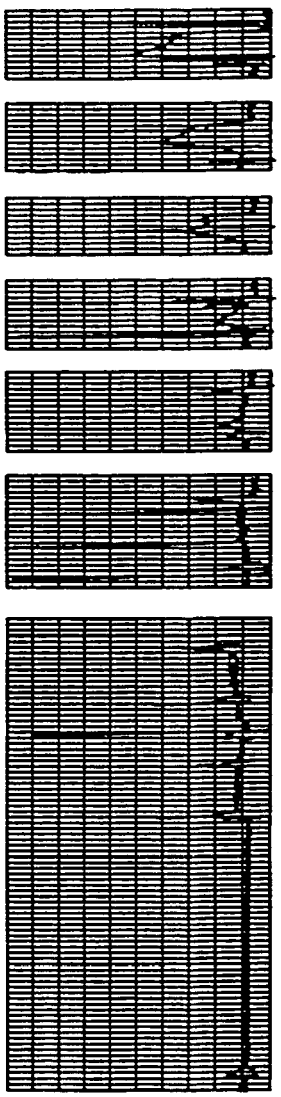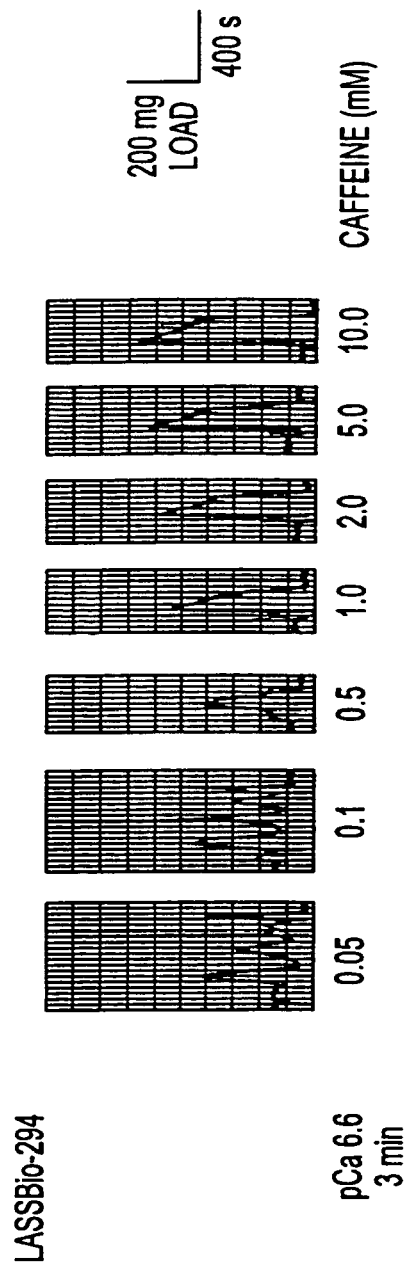
FIG. 10

NEUROMUSCULAR TRANSMISSION IS NOT MODIFIED BY LASSBio-294
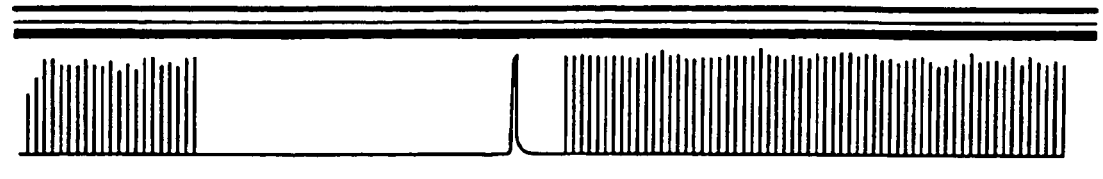
DMSO
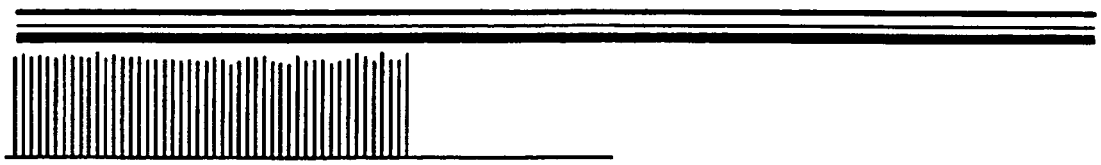
LASSBio-294 1mg.Kg$^{-1}$
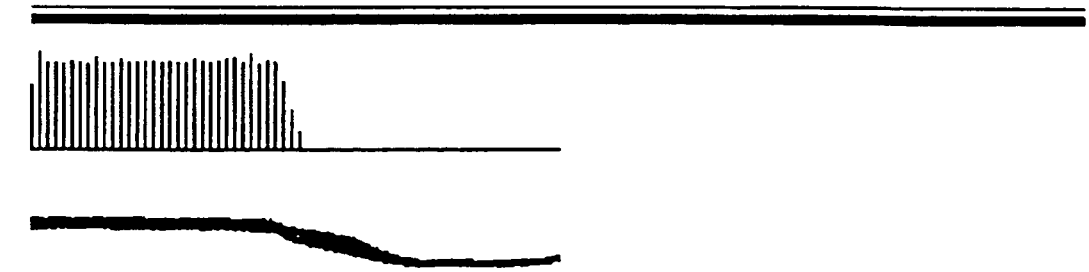
ALLOFERINE 0.6 mg.Kg$^{-1}$
FIG. 31

THIENYLHYDRAZON WITH DIGITALIS-LIKE PROPERTIES (POSITIVE INOTROPIC EFFECTS)

RELATED APPLICATION

The present application is a 371 of PCT/US00/17024 filed Jun. 21, 2000, which claims the priority of U.S. Provisional application 60/140,352 filed Jun. 21, 1999. This application and all references cited herein are hereby incorporated by reference.

FIELD OF THE INVENTION

The invention relates to chemical compounds exhibiting digitalis-like properties and activity, and to methods of making and using this compound. The invention further includes use of these compounds in the treatment of cardiac disease and muscle fatigue. Thus, the invention relates to pharmaceutical compositions containing these compounds. The invention further relates to methods of synthesis of these compounds.

Technology Review

Several drugs in common use, such as digetoxin and digoxin, are derived from digitalis. The common chemical structure of these drugs is a steroid nucleus containing an unsaturated lactone ring and one or more glycoside residues. The mechanism of action of digitalis-derived drugs, or digitalis glycosides, is to selectively inhibit active transport of $K^+$ and $Na^+$, in cardiac muscle, which increases the rate of $Ca^{2+}$ cycling. This has the effect of increasing the velocity and extent of shortening of cardiac muscle by increasing the availability of $Ca^{2+}$ to interact with contractile proteins. Digitalis glycosides also affect the sympathetic nervous system and reduce neurohumeral activation. Examples of currently marketed digitalis glycosides are Lanoxin® and Lanoxicaps® made by Glaxo-Wellcome.

Digitalis glycosides share the property of being toxic immediately above their therapeutic range. Toxic effects of these drugs include: arrhythmias, ECG effects such as increased blood pressure and heart rate, pulmonary congestion, delirium, fatigue, disturbance of color vision, anorexia, nausea, and vomiting. The drugs are cardiotoxic and neurotoxic because of their effect on the sympathetic nervous system. There is significant intra-patient variability in the therapeutic and toxic levels, so that each patient must be individualized to achieve safe therapeutic drug levels. This problem is exacerbated by the fact that many co-administered drugs, such as verapamil, quanidine, and amiodarone, can shift the therapeutic and toxic ranges, requiring additional modification of the dosing regimen. Digoxin is also metabolized by intestinal flora and antibiotic treatment can increase drug bioavailability, causing an overdose.

Thus, the risks due to incorrect dosing of digitalis glycosides are great; and potential effects of overdosing are serious. The treatment for overdose is to bind circulating drug with antibodies to digitalis glycosides. The cost of this treatment can be in excess of $3,000 per incident. An example of such an antibody is Digibind® made by Glaxo-Wellcome. Digibind® is a protein derived from sheep and carries its own risks.

SUMMARY OF THE INVENTION

There is a great medical need for drugs to treat congestive heart failure. Congestive heart failure is an important cause of mortality and morbidity in the U.S.: over 2.5 million patients are currently diagnosed. Compounds derived from digitalis, which are in the class of cardiac glycosides, are the primary drugs used in the treatment of congestive heart failure, particularly systolic dysfunction. However, digitalis ameliorates congestive heart failure by producing a positive inotropic effect. A positive inotropic agent strengthens the contractility of muscular tissue. Digitalis-derived drugs have the defect of being cardio-toxic and neuro-toxic at doses just above their therapeutic range (Hardman, J. G. and Limbird, L. E., *The Pharmaceutical Basis of Therapeutics,* 9$^{th}$ ed. McGraw-Hill New York, 1996, chapter 34). There is a need for drugs that can treat congestive heart failure and are less toxic near their therapeutic range.

The invention includes the novel chemical compound having the formula (I)

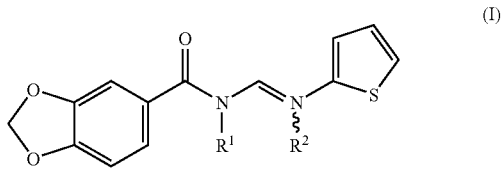

In formula (I), each of $R_1$ and $R_2$ is hydrogen, alkyl of 1 to 6 carbon atoms, phenyl and substituted phenyl. Preferably at least one of $R_1$ or $R_2$ is hydrogen.

The invention further includes the synthesis of a novel compound that, like digitalis, produces a positive isotropic effect on cardiac and skeletal muscle. Like digitalis, it has utility in the treatment of congestive heart failure. Unlike digitalis, it does not have toxic properties near its effective therapeutic range and therefor the invention has a medical advantage over that class of drugs. The invention has further utility in the treatment of muscle fatigue in pathological states.

The invention compound(s) act(s) as a calcium sensitizer in heart and skeletal muscle. It delays and shortens fatigue of skeletal muscle and thus also has utility in the treatment of muscle fatigue. Muscle fatigue is a symptom of certain pathological states such as: major injury, cancer, HIV infection, sepsis, Crohn's disease, ulcerative colitis, and athletic over-training.

BRIEF DESCRIPTION OF THE FIGURES

FIG. 1. Table 1. Histopathological Study of Tissues and Organs of Rats Injected with BASSBio-294. Table 2. Toxicity Study of LASSBio-294 Injected in Mice. Weight of mice in grams. Table 3. Blood Cell Analysis in Mice Treated with LASSBIO-294. Table 4. Blood Biochemistry Analysis in Mice Exposed to LASSBio-294. Table 5. Measurements of the time parameters described in FIG. 24. The first column shows the numbers done in control experiments (DMSO) or in 25 µM of compound 294. The last line is the ratio between the values obtained in compound 294 and the control experiments in Ringer plus DMSO.

FIG. 10. Calibration: Vertical, 10 mm=20 mg; Horizontal, 10 mm=40 sec.

FIG. 31. Records of contractions of rat gastrocnemius muscles induced by stimulation of the sciatic nerve and of arterial pressure. For control, contraction was induced by intravenous injection of DMSA (0.04 ml). LASSBio-294 was administered in DMSO. As a test of the functionality of the model, the depression of muscle contraction induced by alloferine was recorded.

DETAILED DESCRIPTION OF THE INVENTION

Figure 2:
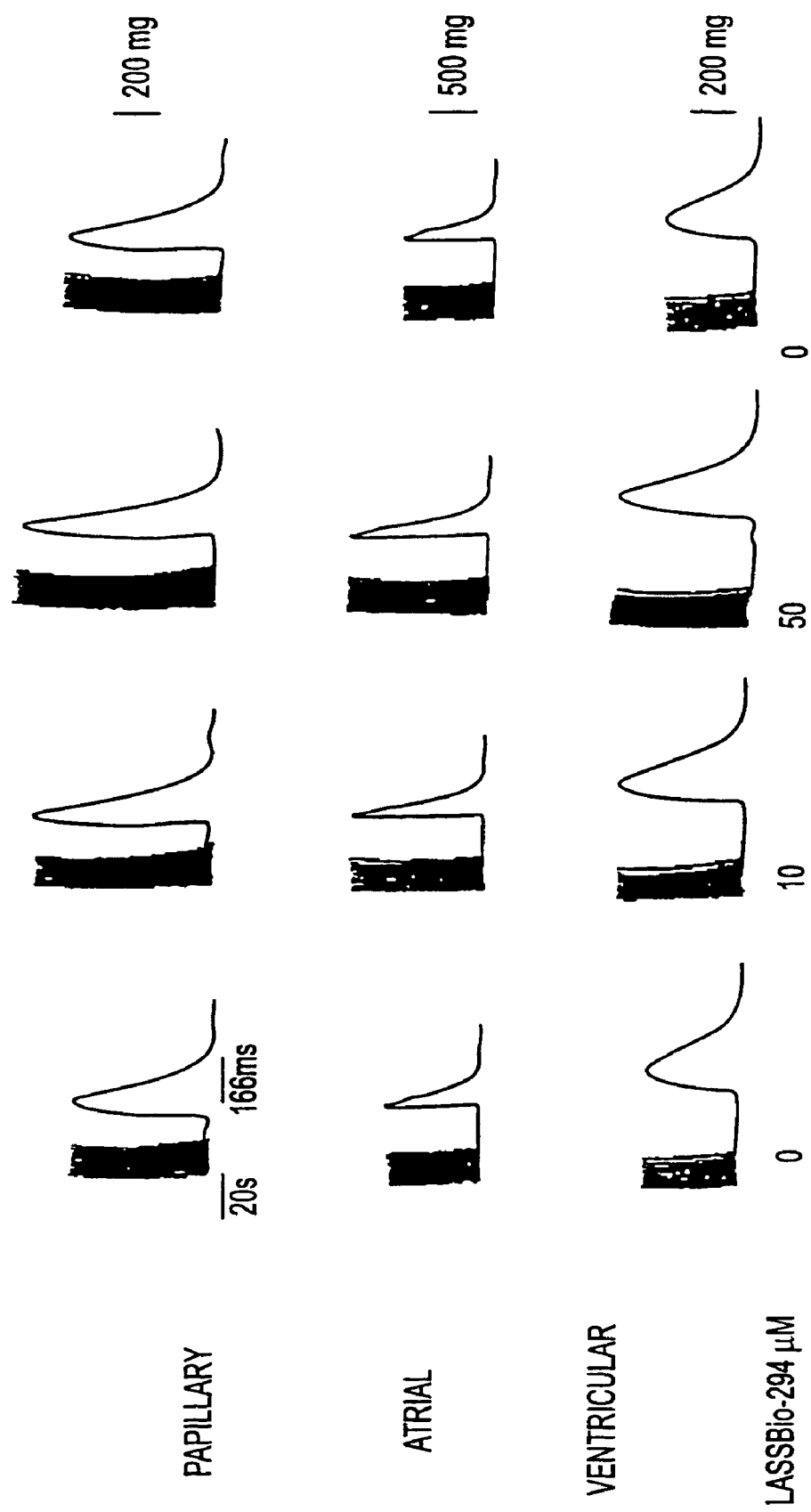
FIG. 2. The papillary muscle, and bundles of atrial and ventricular cells obtained from rat hearts were dissected and set in an aerated chamber to enable recording of isometric tension. LASSBio-294 was added to the chamber in a cumulative manner, first 10 µM and increasing to 50 µM and recordings made after allowing 5 min. for equilibration.

A compound of the invention, like digitalis, produces a positive isotropic effect on cardiac and skeletal muscle. Like digitalis, it has utility in the treatment of congestive heart failure. Unlike digitalis, it does not have toxic properties at its effective therapeutic dosage levels; and, therefor, the invention provides a medical advantage over that class of drugs. A compound of the invention has further utility in the treatment of muscle fatigue in pathological states. The invention acts as a calcium sensitizer in heart and skeletal muscle and it delays and shortens fatigue of skeletal muscle and thus also has utility in the treatment of muscle fatigue. Muscle fatigue is a symptom of certain pathological states such as: major injury, cancer, HIV infection, sepsis, Crohn's disease, ulcerative colitis, and athletic over-training.

The invention includes the novel chemical compound having the formula (I)

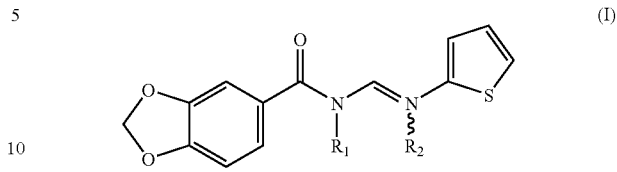

Each of $R_1$ and $R_2$ is a substituent selected from the following in any combination: hydrogen, alkyl of 1 to 6 carbon atoms phenyl, and substituted phenyl. Preferably, at least one of $R_1$ or $R_2$ is hydrogen. In a preferred embodiment, each of $R_1$ and $R_2$ I hydrogen; and then the compound has formula (II):

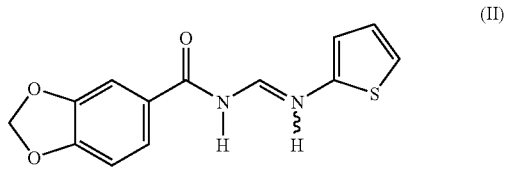

The compound of formula (II) is 3,4-methylenedioxybenzoyl-2-thienylhydrazone and has been designated LASSBio-294.

The invention further includes pharmaceutically acceptable salts of the compounds of formula (I) and (II). Such salts can include the acetate, citrate, phosphate, fumarate, benzoate, tartrate, succinate, chlorate, sulfate, butyrate, stearate, palmitate, lactate, methylate, and carbonate salts. These salt forms can be prepared by reacting the compound with appropriate acids under standard conditions.

In accordance with the present invention, a compound of formula I, and particularly of formula II, can be a potent, positive inotropic agent for cardiac and skeletal muscle. It is within the scope of the invention to use the invention compound(s) to increase the strength of heart muscle contraction. A compound of formula II can be used, like cardiac glycosides, to treat congestive heart failure. In another aspect, the invention encompasses the effects of the compound on skeletal muscle; and its use in the therapeutic treatment of muscle fatigue. Muscle fatigue is a serious complication of certain pathological states.

The synthesis of compounds of formulas (I) and (II) from safrole is described in the following steps. Although the techniques used and some of the intermediates in the synthesis are known, the use of these techniques to produce this novel compound is itself novel in the art. The synthesis uses as the starting material, safrole, (4-allyl-1,2-methyldioxybenzene). Safrole is the principal constituent of sassafras oil, from which it is readily isolated. It is also available from commercial sources.

The compound of formula (I) and (II) is synthesized from the starting material safrole by means of the following scheme; technical details of the synthetic method are provided in CHEMICAL EXAMPLE 1.

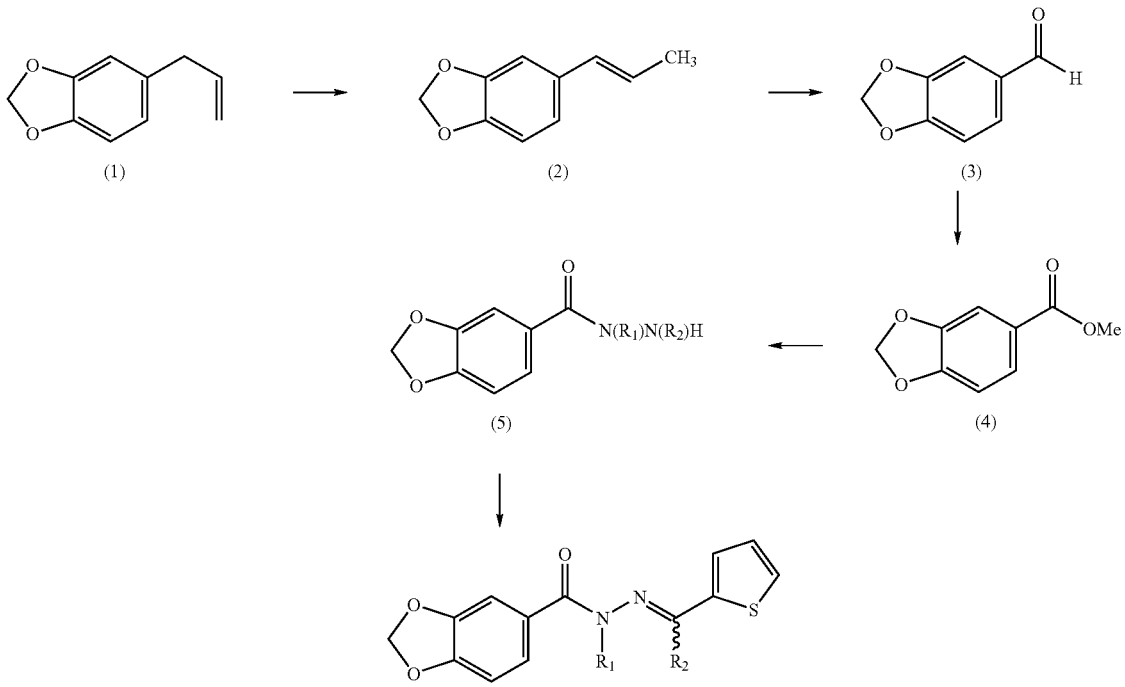

In the formula (II) compound each of $R_1$ and $R_2$ is hydrogen.

The invention includes the novel chemical compound having the formula (I) Compounds of formula (I) may contain substitution on the 2 and/or 5 and/or 6 position of the benzoyl moiety and/or on the thienyl moiety in the 2 and/or on the 3 and/or 4 position(s) of the thienyl moiety. Thus, $R_3$, $R_4$, $R_5$, $R_6$, $R_7$, and $R_8$ may be hydrogen, alkyl of 1 to 6 carbon atoms, phenyl [unsubsituted or substituted], amino [secondary, tertiary or quaternary amino], nitro-, ester [RCOO—], acid [—COOH, alcohol [—OH] or ether [RO—], to form compounds of the following structure (III):

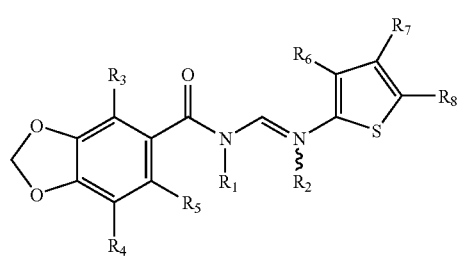

wherein each of R3–R8 is as defined above.

Pharmaceutical compositions of the invention comprise a compound of formula (I), formula (II) and/or of formula (III). The dose range for the compound of formula (II), based on in vitro and in vivo tests, is one that produces between levels of 100 μM and 500 μM in plasma, a more effective dose produces between levels of 1 μM and 100 μm, the most effective dose produces between levels of 20–50 μM in plasma. This plasma concentration can be achieved in several ways depending on the therapeutic requirements of the patient.

Dosage forms that target alternative routes of administration are within the scope of the invention. The exact form of the dosage of pharmaceutical compositions of the invention can be established by such experimentation as one of skill in the art would normally undertake and by the requirements of the clinical situation to be treated. A parenteral form can be used for intravenous and intramuscular infusion. This can be supplied as either a powder or a concentrate to be used as a solution at the time of dosing or as an injectable, sterile solution. The diluent could be water, saline, or a lipid based diluent containing ethanol and buffers such as citrate to stabilize pH, and preservatives such as sodium benzoate and methylparaben, as required. The diluent could further contain such other excipients and could contain pharmaceutically acceptable carriers as may be desirable such as a protein carrier, including serum albumen. The invention also encompasses the use of solvents such as dimethyl sulfoxide (DMSO), alcohol, ethylene glycol or polyethylene glycol. Such solvents can be used alone or in combination. A nasal spray is also encompassed by the invention and could readily be compounded by one of skill in the art using such diluents and inactive ingredients as are commonly used. Solutions can be emulsions or micro-emulsions containing an oily phase, an aqueous phase, and optionally a surfactant. The oily phase can contain one or more of the following: carboxylic acid esters, fatty acids, fatty esters, glyceryl derivatives such as glyceryl behenate, short, medium and long chain triglycerides, and others. Surfactants that may be used with the invention to produce a pharmaceutically acceptable formulation include polyoxyethylene sorbitan esters, ethyleneoxide propylene oxide block co-polymers, polyglycolized glycerides, sucrose esters, polyoxyethylene laurel esters, and others.

It is within the scope of the invention to formulate the pharmaceutical compositions of the invention in tablet form. One of skill in the art can readily formulate such a tablet using inactive ingredients such as cellulose, microcrystalline cellulose, corn starch, lactose, starch, silica, dextrose and stearic acid, and such additional ingredients as dis-integrants, including carboxy methyl cellulose, soy polysaccharides, pre-gelatinized starches, and polyethylene glycol and lubricants to achieve a pharmaceutical preparation that can be readily manufactured. Such lubricants can include polyethylene glycol, leucine, glycerol behenate, magnesium stearate, or calcium stearate. Similarly, the pharmaceutical composition of the invention can be used as a hard or soft gelatin capsule in combination with suitable inactive ingredients such as lactose, cornstarch, microcrystalline cellulose, soy polysaccharides, calcium phosphate dihydrate, calcium sulfate, lactose, sucrose, sorbitol, or suitable liquids or gels. The tablet or capsule could readily be coated. Such a coating could be an enteric coating to provide for intestinal release of the drug, or a neutral coating to improve stability of the tablet or capsule.

As a drug pharmaceutical compositions of the invention can also be provided as an elixir for pediatric and geriatric dosing. Such an elixir could readily by formulated by one of skill in the art and could contain water, ethanol, solvents and surfactants as well as a preservative, such as methyl paraben, citric acid, and coloring and flavoring ingredients, as desired. A rectal suppository is also with in the scope of the invention and could be readily compounded using standard methods. Such a suppository could contain waxes, oils, lipids or gelling agent to produce a stable formulation which melts at body temperature. It could contain such solubilizers, surfactants, and stabilizers as might be required.

Other routes of administration such as buccal, sublingual, transdermal, and subcutaneous are within the scope of the invention. Such form of administration might be preferred when a treatment was needed with rapid effectiveness or when the patient has difficulty swallowing. Any of the dosage forms described could be formulated as an immediate, sustained or delayed release form. The compound could be administered as a single dose, multiple doses, or a continuos dose over a time period depending on the therapeutic need.

If the therapeutic situation requires it, it is within the scope of the present invention to create a pro-drug of LASSBio294. Such a molecule would combine LASSBio-294 with a carrier molecule, for example a dipeptide, tripeptide, or any molecule absorbed in the intestine via transporter-mediated transport, so as to increase the bioavailability of the drug in oral formulation.

Various tests on whole animals and in isolated hearts and muscle fibers have been carried out, which show that the invention produces reactions that can be correlated with positive inotropic activity in humans. These tests indicate that LASSBio-294 will have therapeutic utility in the treatment of disease states. Whole animal and in vitro models are known in the art to predict of the behavior of drugs in humans, including drugs used in the treatment of congestive heart failure. (Hoffmeister, H. M., Beyer, M. E., and Oeipel, L. (1997) Am. J. Cardiol. 80, 25G; Remy-Jouet, I., Cartier, F., Lesouhaitier, O., Kuhn, J. M., Fournier, A., Vaudry, H., Delaure, C., (1998) Horm. Metab. Res. 30, 341, each of these references being expressly incorporated by reference herein).

One such predictive test is the test of isometric tension in rat cardiac muscle. LASSBio-294 has a positive effect on contractility of cardiac muscle. It increases the isometric tension achieved by isolated bundles of muscle. Ventricular, papillary and atrial cardiac muscle bundles all achieved increased tension up to a 2-fold over control, when treated with LASSBio-294 at concentrations of up to 200 uM. This test predicts that the invention will have positive inotropic effects in human cardiac muscle.

Predictive tests can also be performed on isolated hearts of animals. Testing intraventricular and arterial pressure in isolated dog hearts, under pre-load, is an animal model for human congestive heart disease, as is well known in the art. This is called Langendorff's method. It allows examination of therapeutic strategies to treat congestive heart disease. When dog hearts were so tested, LASSBio-294 treated hearts achieved a 50% increase in intraventricular and aortic pressure compared to control or wash out after treatment. The electro-cardiogram (ECG) of isolated rat heart, without pre-load, showed no change after treatment with LASSBio-294. When LASSBio-294 was tested on intact, anesthetized dogs with normal cardiac function and no pre-load, there was no change in pressure after injection of LASSBio-294. These tests predict that the invention has utility as a medicament in the treatment of congestive heart failure (Curtis, M. J., (1998) Cardiovasc. Res. 39, 194–21, incorporated expressly by reference herein).

Another predictive test can be performed on isolated cardiac muscle fibers. The mechanism of action of LASSBio-294 was determined by examining the sarcoplasmic reticulum of cardiac muscle fibers. Tests showed that treatment with LASSBio-294 increases uptake of $Ca^{2+}$. Further tests demonstrated that LASSBio-294 increases the storage of $Ca^{2+}$ by the sarcoplasmic reticulum. Thus, the mechanism of action of LASSBio-294 is different from cardiac glycosides, which act by inhibiting active transport of $Na^+$ and $K^+$. LASSBio-294 increases bioavailability by increasing the storage of calcium in the sarcoplasmic reticulum (SR); it does not change the sensitivity of muscle fibers to calcium. The tests were performed on human skeletal as well as rat cardiac muscle fibers. These tests predict how LASSBio-294 will achieve its therapeutic effects in human cardiac and skeletal muscle (Weir, W. G. and Hess, P., (1984) J Gen. Physiol., 83, 395). LASSBio-294 treated skeletal muscle fibers showed increased resistance to muscle fatigue compared to control fibers. Neuromuscular transmission was unaffected by LASSBio-294. Supportive tests were also successfully performed in amphibians. These tests predict a second therapeutic use of LASSBio-294 in the treatment of muscle fatigue (Albuquerque, E. X., Daly, J. W., Warnick, J. E. (1988) Ion Channels, 1, 95; Gallant, E. M., Godt, R. E., and Gronert, G. A., (1980) J. Pharmacol. Exp. Ther. 213, 91).

LASSBio-294 has very low toxic effects. This was tested in whole mouse, rat, and dog models (Greaves, P. (1998) Exp. Toxicol. Pathol. 50, 283). These models are commonly used to predict toxicity in humans (Chou, W. L., Robbie G., Chung, S. M., Wu, T. C., and Ma, C. (1998) Pharm. Res. 15, 1474). Major tissue types and organs were unaffected by LASSBio-294 given in doses greater than those which showed inotropic activity, and animal weights and blood cell counts were unaffected. The LD 50 in dogs is 1.5 g/kg, an amount more then 1000 fold greater than the effective dose. These tests predict LASSBio-294 can be dosed in humans to achieve therapeutic plasma levels without significant risk of toxicity.

Definitions

Calcium sensitizer: An agent that increases the $Ca^{2+}$ and/or the amount of $Ca^{2+}$ available. Congestive heart failure: Heart failure in which the heart is unable to maintain an adequate circulation of blood in the bodily tissues or to pump out the venous blood returned to it by the veins.

Langendorff's method: The experimental method using perfusion of the isolated mammalian heart by carrying fluid under pressure into the sectioned aorta, and thus into the coronary system.

Muscle fatigue: Temporary loss of power to respond induced in a muscle by continued stimulation. This symptom is found in patients with HIV infection, cancer, major injuries, sepsis, Crohn's disease, ulcerative colitis, chronic fatigue syndrome, and to some extent in over-trained athletes.

Positive inotropic agent: an agent that strengthens the contractility of muscular tissue.

Pharmaceutically or therapeutically acceptable carrier: a carrier medium which does not interfere with the effectiveness of the biological activity of the active ingredients and which is not toxic to the host or patient.

EXAMPLES

Chemical Examples

Example 1

The synthesis of LASSBio-294 from safrole is described in the following steps. Although the techniques used and some of the intermediates in the synthesis are known, the use of these techniques to produce this novel compound is itself novel in the art.

The synthesis uses safrole, (4-allyl-1,2-methyldioxybenzene) as starting material or reagent. Safrole is the principal constituent of sassafras oil, from which it is readily isolated. It is also available from commercial sources.

LASSBio-294 is synthesized from safrole following the following scheme.

Numbers below each structure refer to the number before each step in the following synthesis. The molecule numbered is the starting material for that step and is reacted to form the next molecule. Clearly the invention is not limited to the following synthesis scheme but also encompasses all such variations and modifications as will be clear to one of skill in the art to produce similar results.

(1) Synthesis of isosafrale To 80 g (0.49 mmol) of safrole was added 100 ml of a 3N solution of potassium hydroxide (KOH) in n-butyl alcohol and the reaction mixture was stirred at room temperature for 3 h. The mixture was poured into a solution of 12 ml of concentrated hydrochloric acid (HCl), and 52 ml of ice water. After neutralization with additional concentrated HCl, the organic layer was extracted with three 35-ml portions of ethyl acetate. The organic extracts were treated with brine, dried over anhydrous sodium sulfate and concentrated under reduced pressure, furnishing a crude oily residue. Distillation of this residue, under reduced pressure, furnished 78.4 g (97%) of isosafrole, as a colorless oil.

(2) Synthesis of Piperonal A solution of isoafrole (2 g, 12.1 mmol) in acetic acid (10 ml) was saturated with ozone at 0° C., until the formation of a slight blue color. After removal of the excess of ozone by bubbling $N_2$ through for some time, the ozonide was decomposed by stirring in the presence of zinc (Zn) (5 g, 0.076 atg) at 0° C. for 2 h. After filtration, ethyl acetate was added, the reaction mixture was washed with water, and the solvent was evaporated, following which it was dried over anhydrous sodium sulfate, affording 1.42 g (77%) of piperonal, as a white solid, m.p. 36–37° C.

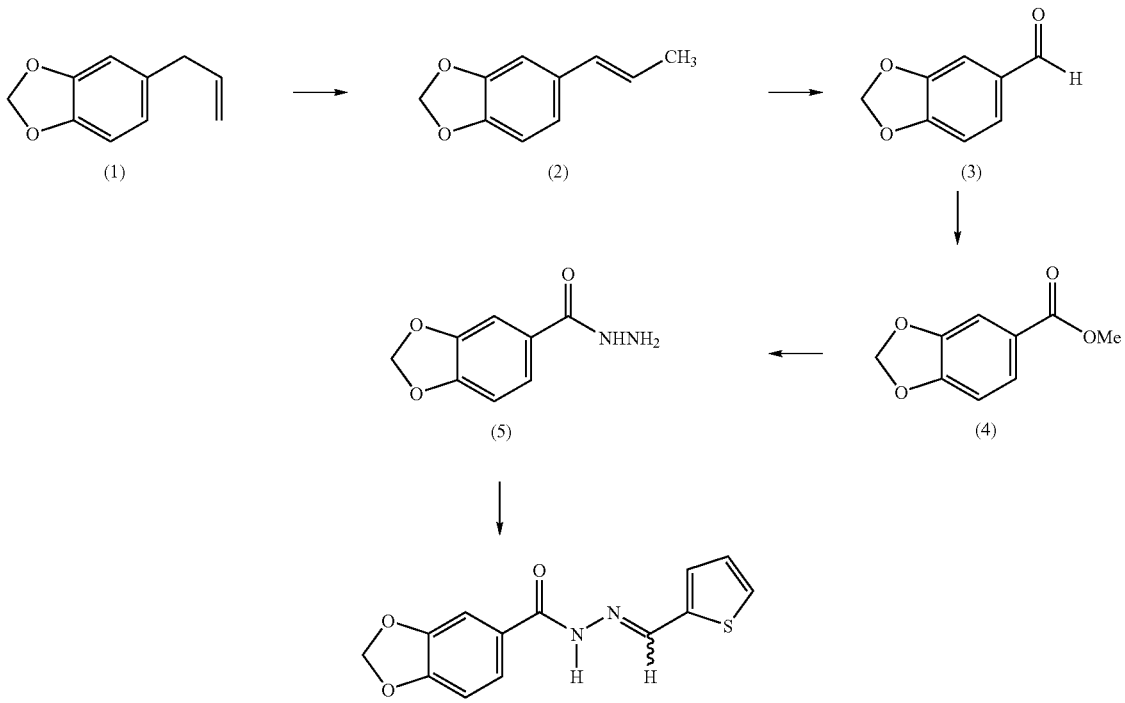

LASSBio-294

(3) Synthesis of Methyl 3,4-Methylenedioxybenzoate To a solution of piperonal (0.30 mmol 0.045 g) in absolute methanol (4 ml) cooled at 0° C., were successively added methanolic solutions (each 3 ml) of iodine (0.100 g, 0.39 mmol) and KOH (0.440 g, 7.85 mmol) at 0° C. After stirring for 1.5 hour at 0° C., small amounts of saturated $NaHSO_3$ solution were added until the disappearance of the brown color. Next, the methanol was almost totally evaporated under reduced pressure. To the residue was added water and the desired methyl 3,4-methylenedioxybenzoate was obtained by filtration, in 90% yield, as a white solid m.p. 53° C.

$^1$NMR (200 MHz) $CDCl_3$/TMS (δ-ppm): 7.63 (dd, $H_6$, Jax-8.2 Hz, Jbx=1.7 Hz); 7.44 (d, $H_2$, Jax=1.6 Hz); 6.82 (d, $H_5$, Jax=8.2 Hz); 6.02 (s, O—$CH_2$—O); 3.87 (s, O—$CH_3$); $^{13}$C NMR (50 MHz) $CDCl_3$/TMS (δ-ppm); 166.0 (C=O); 151.4 ($C_4$); 147.5 ($C_3$); 125.1 ($C_6$); 124.0 ($C_1$); 109.3 ($C_2$—AR); 107.7 ($C_5$); 101.6 (O—$CH_2$—O); 51.9 ($OCH_3$); M.S. (70 eV) m/z (relative abundance); 180 (50%); 149 (100%), 121 (20%); 91 (8%), 65 (18%); IR (KBr) $cm^{-1}$: 1723 (C=O); 1289 (C—O).

(4) Synthesis of 3,4-Methylenedioxybenzoylhydrazine To a solution of 2.67 g (14.85 mmol) of methyl 3,4-methylenedioxybenzoate in 10 ml of ethanol, was added 15 ml of 80% hydrazine monohydrate. The reaction mixture was maintained under reflux for 3.5 hours, when thin layer chromatography indicated the end of the reaction. Then, the media was poured on ice, and the resulting precipitate was filtered out, affording the 3,4-methylenedioxybenzoylhydrazine derivative in 70% yield, as a white solid, m.p. 170–171° C.

$^1$H NMR (200 MHz) DMSO/TMS (δ-ppm): 10.74 (s, —CONH—); 7.44 (dd, $H_6$, Jax=8.2 Hz, Jbx=1.6 Hz); 7.36 (s $H_2$) 7.17 (d, $H_5$,J=8.2 Hz); 6.10 (s, O—$CH_2$—O); 4.45 (s, —$NH_2$); $^{13}$C NMR (50 MHz) DMSO/TMS (δ-ppm); 165.2 (C=O); 149.6 ($C_4$); 147.3 ($C_3$); 127.2 ($C_1$); 121.9 ($C_8$); 107.9 ($C_2$); 107.1 ($C_5$); 101.6 (O—$CH_2$—O); M.S. (70 eV) m/z (relative abundance); 180 (17%); 149 (100%), 121 (25%); 91 (8%); 65 (19%); IR (KBr) $cm^{-1}$: 3303.9 NH2); 3220 (NH); 1605 (C=O); 1262 (C—O).

(5) Synthesis of 3,4-Methylenedioxybenzoyl-2-thienylhydrazone (LASSBio-294) To a solution of 0.150 g (0.83 mmol) of 3,4-methylenedioxybenzoylhydrazine in absolute ethanol (7 ml) containing two drops of 37% hydrochloric acid, was added 0.098 g (0.87 mmol) of thiophene-2-carboxaldehyde. The mixture was stirred at room temperature for 30 minutes, after which extensive precipitation was visualized. Next, the mixture was poured into cold water, and the precipitate formed was filtered out and dried. The 3,4-methylenedioxybenzoyl-2-thienylhydrazone was obtained in 85% yield, after recrystallization in ethanol, as yellow needle crystals, m.p. 204–205° C.

$^1$NMR (200 MHz) DMSO/TMS (δ-ppm): 11.53 (s, —CONH—); 8.62 (s, =CH—); 7.65 (d, $H_5$, J=5.0 Hz); 7.53 (d, $H_4$, J=5.0 Hz); 7.50 (dd, $H_6$, Jax=8.2 Hz, Jax=8.2 Hz, Jbx=0.8 Hz); 7.41 (s, H2); 7.12 (dd, H3', Jax=4.8 Hz, Jbx=3.9 Hz); 6.12 ($s_1$ O—$CH_2$—O); $^{13}$C NMR (50 MHz) DMSO/TMS (-ppm); 162.1 (C=O); 150.2 ($C_4$); 147.4 ($C_3$); 142.6 (=Ch—); 139.2 ($C_{1'}$); 130.8 ($C_{3'}$); 128.8 ($C_{2'}$); 127.9 (C4'); 127.1 (C1); 122.8 (C8); 108.0 (C2); 107.6 (C5); 101.8 (O—CH2—O); IR (KBr) $cm^{-1}$: 3075 (NH); 2798 (N=CH); 1610 (C=O); 1540 (C=N); 1275 (C—O).

Detailed technical methods for performing the described steps can be found in the following references (Barreiro, E. J. and Lima, M. E. F (1992) *J. Pharm. Sci.* 81, 1219); (Barreiro, E. J., Costa, P. R., Coelho, F. A. S. and Farias, F. M. C. (1985) *J. Chem. Res.*, (M) 2301.); (Yamada, S., Morizono, D., Yamamoto, K. (1992) *Tetrahedron Lett.*, 33, 4329); (Dias, M. L. R., Alvim, J. J. F., Freitas, A. C. C., Barreiro, E. J., Miranda, A. L. P. (1994) *Pharm. Acta Helvetiae*, 69, 163.).

Pharmaceutical Examples

Example 1

Toxicity a. Table 1 shows a histo-pathological table of rat tissues and organs examined after the animal had been treated with LASSB-294. The table shows that there were no pathological changes in the tissues and organs examined after LASSBio-294 injection.

b. Rats were weighed before and after treatment with LASSBio 204. Table 2 shows weights of mice in grams after injection with LASSBio294, compared to saline and solvent vehicle controls. Six rats were examined in each group, measurements were made after 1–15 days of treatment. The data show that there is no change in weight in any group during the test period.

c. Mice were injected with LASSBio-294 and their blood examined for cell changes. Experimental groups received 2 or 10 mg/kg of drug. Table shows no significant change in blood cell values for any group. Hematocrit levels, leucocytes and hemoglobin were not significantly changed by LASSBio-294 (Table 3).

d. Table 4 lists blood chemistry analysis of mice treated with LASSBio-294. Experimental groups received 2 or 10 mg/kg of drug. Controls were saline and solvent. The data show no significant change in blood chemistry values for any group. The low values of glucose found could be due to an artifact of the technique, glucose being a byproduct of hemolysis. In male and female mice, subjected to long-term treatment with the compound, tests of hemoglobin, erythrocytes and blood biochemistry again showed values similar to control.

General Method

To test for possible systemic toxicological changes induced by LASSBio-294, animals were divided into four groups, control (saline), solvent (dimethylsulphoxide (DMSO)/polyethylene glycol (PEG), LASSBio-294 2 mg/kg, and LSSBio-294 10 mg/kg. Animals were injected daily for more than 14 days. The results show that LASSBio-294 at concentrations that produce significant positive inotropic effect on the heart muscle produces no significant histopathological changes in the organ and tissues studied.

Example 2

Figure 3:
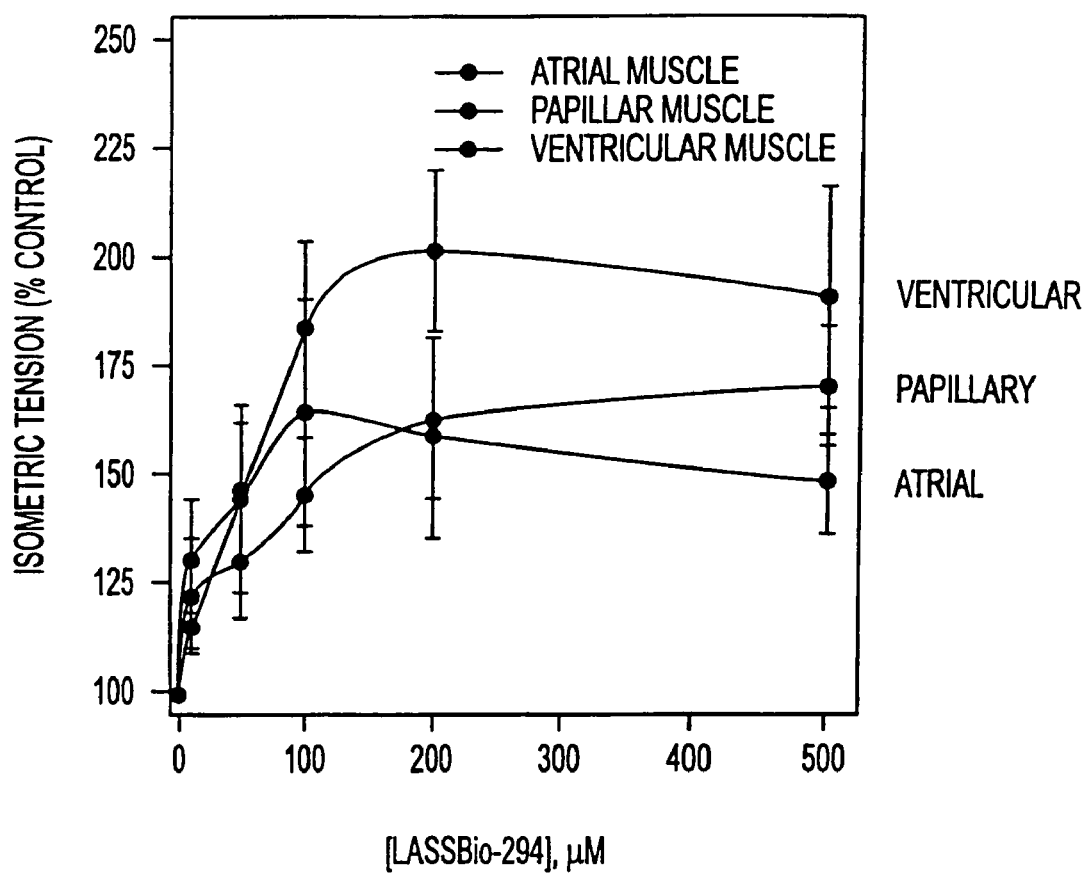
FIG. 3. LASSBio-294 was added to the physiologic solution at increasing concentrations. The isometric tension was expressed as a percent of control, as measured prior to addition of test solution. N=9 for each concentration.

Isometric Tension in Cardiac Muscle a. The test shown in FIG. 2 measured the effect of LASSBio-294 on the isometric tension of papillary, atrial, and ventricular bundles of rat cardiac muscle. Chart traces are of muscle tension for each muscle group. All muscle groups show an increase in tension after 10 μM and 50 μM of LASSBio-294.

b. FIG. 3 contains a graphic representation of the effect of LASSBio-294 on isometric tension of papillary, atrial, and ventricular bundles of rat cardiac muscle. LASSBio-294 at concentrations of 0 μM, 25 μM, 50 μM, 100 μM, 200 μM, and 500 μM was used. Isometric tension is expressed as a percent of control that was measured prior to addition of the test solution. Isometric tension increased for each concentration up to 200 μM. FIG. 3 shows the accumulated results of nine tests for each concentration.

General Method

The papillary muscle, and bundles of atrial and ventricular cells obtained from rat hearts were dissected and set in an aerated verticle chamber to enable recording of isometric tension. LASSBio-294 was added to the chamber in a cumulative manner. Recordings made after allowing 5 min. for equilibration.

Example 3

Figure 4:
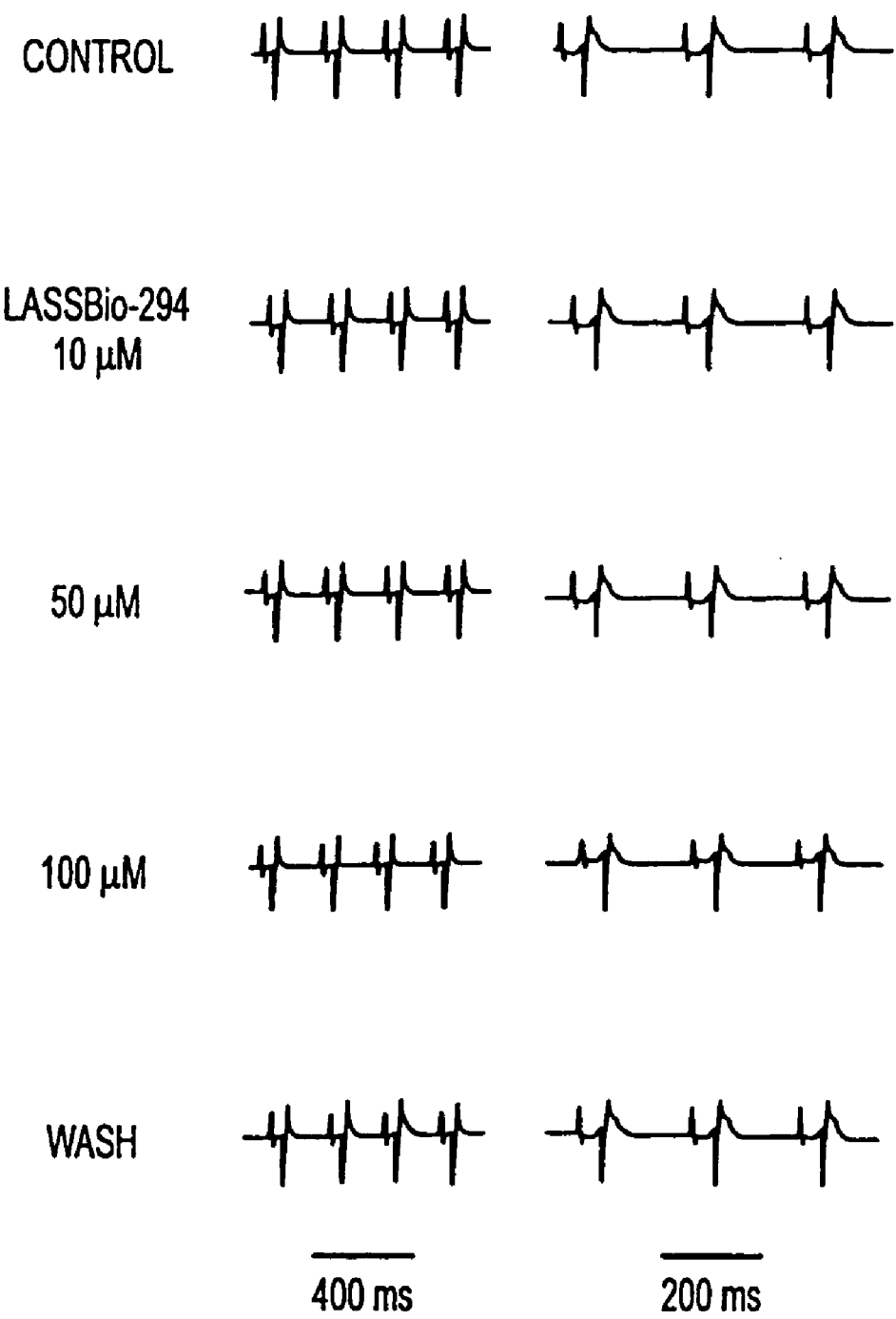
FIG. 4. Hearts of adult rats were quickly removed and placed in an aorta retrograde perfusion system (modified Langendorrff) for measurement of electrocardiogram (ECG).
Figure 5:
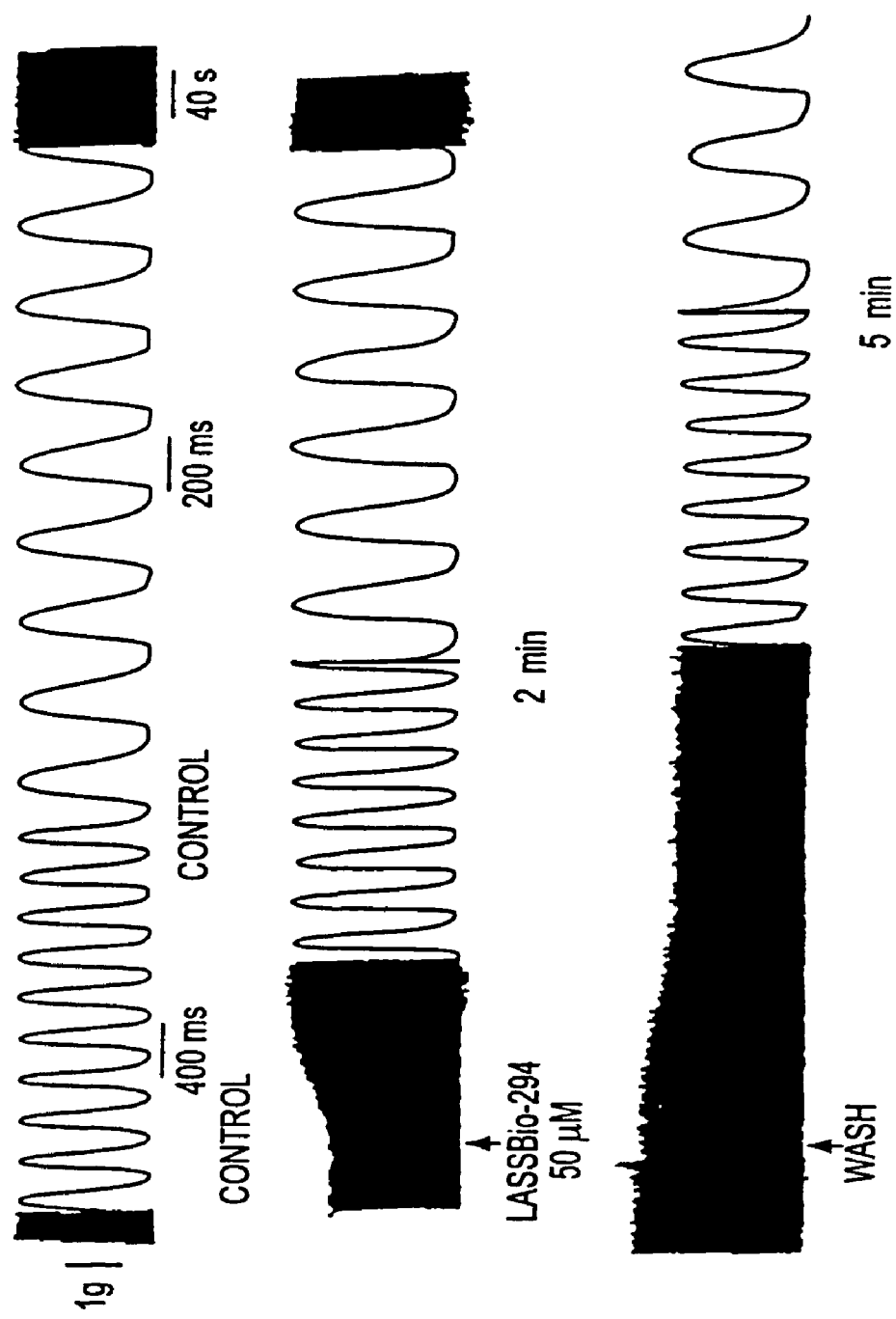
FIG. 5. Recordings of twitch tension in isolated hearts. Control (top), LASSBio-294 (middle) and wash (bottom).

Isolated Hearts a Recordings of electrocardiogram (ECG) of isolated rat heart are shown in FIG. 4 which compare control, LASSBio-294 treatment, 10 uM, 50 μM and 100 μM and post-treatment wash. No treatment had any effect on ECG. These data indicates that LASSBio-294 does not cause abnormal ECG even at dose levels that show increased isometric tension.

b. FIG. 5 illustrates a test of change in isometric tension induced by LASSBio-294 in isolated hearts under preload. Concentration of LASSBio-294 in the bathing solution is 50 μM, which is half of the highest concentration tested in the ECG tests described in FIG. 4. Hearts were treated under a pre-load of 1 g; control was compared to LASSBio-294 and wash. LASSBio-294 treated hearts demonstrated an increase in isometric tension compared to control. This effect was lost in the wash out period. The pre-load tension test is considered to be an animal model of congestive heart disease. Comparing the effect of drugs with this test is predictive of therapeutic effect of treatment in human congestive heart disease.

General Method

Hearts were quickly removed and placed in an aorta retrograde perfusion system for measurement of ECG. Increasing concentrations of LASSBio-294 were added to the bathing solution. The system equilibrated for 5 min. before measurement of isometric tension after each addition.

Example 4

Whole Animal Testing

Figure 6:
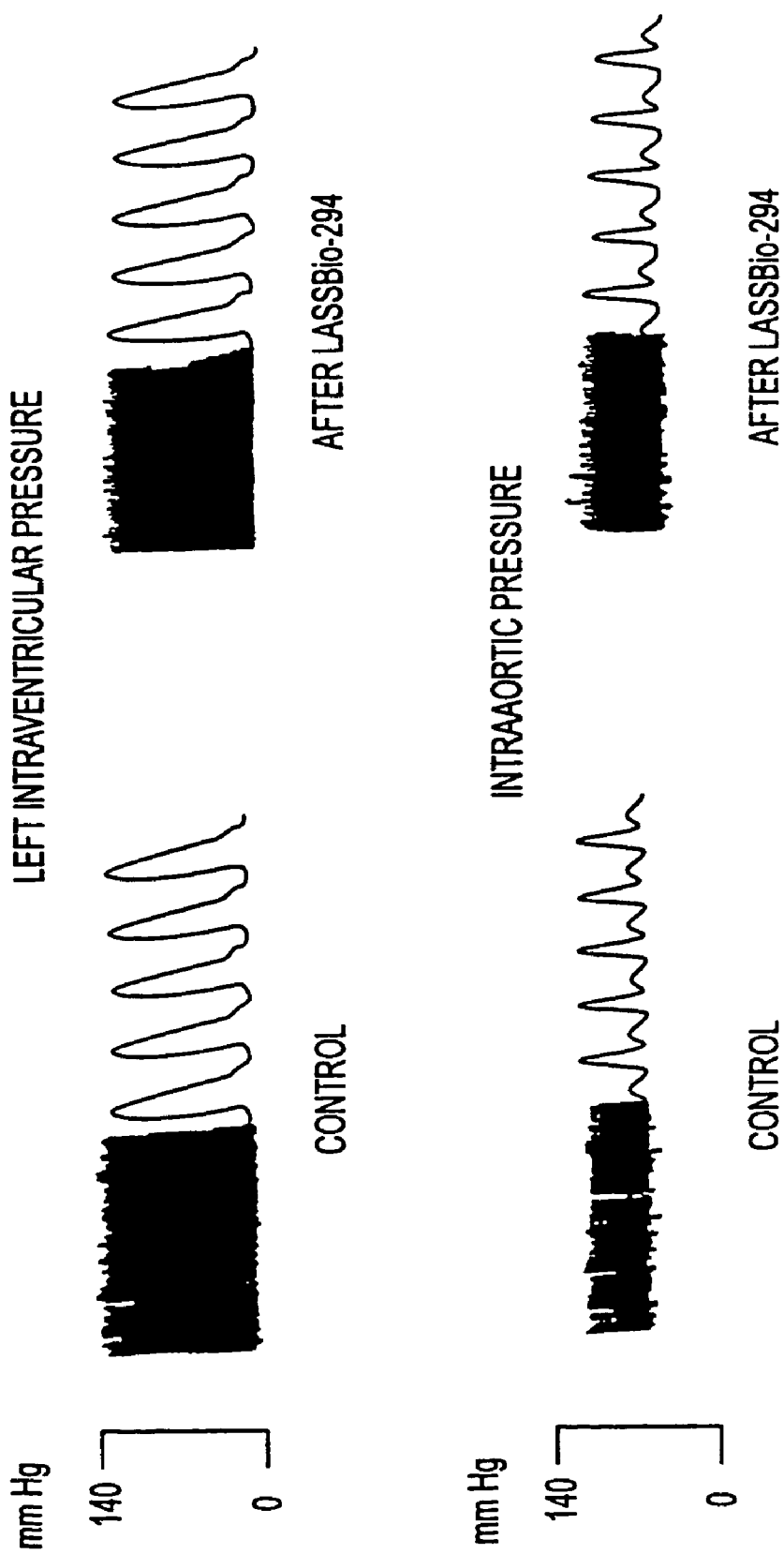
FIG. 6. Recording of left intraventricular pressure and arterial pressure in dogs anesthetized and ventilated normally.

FIG. 6 illustrates a test that measured pressure from the hearts of intact dogs during LASSBio-294 application. Recordings were made of left intraventricular pressure and arterial pressure. These measures show no change with LASSBio-294 application indicating that, in dogs without congestive heart failure, the compound had no significant inotropic effect.

General Method

Dogs were anesthetized and normally ventilated. Recordings were made before and after application of LASSBio-294, 1 mg kg$^{-1}$ min$^{-1}$ for 13 min.

Example 5

Figure 7:
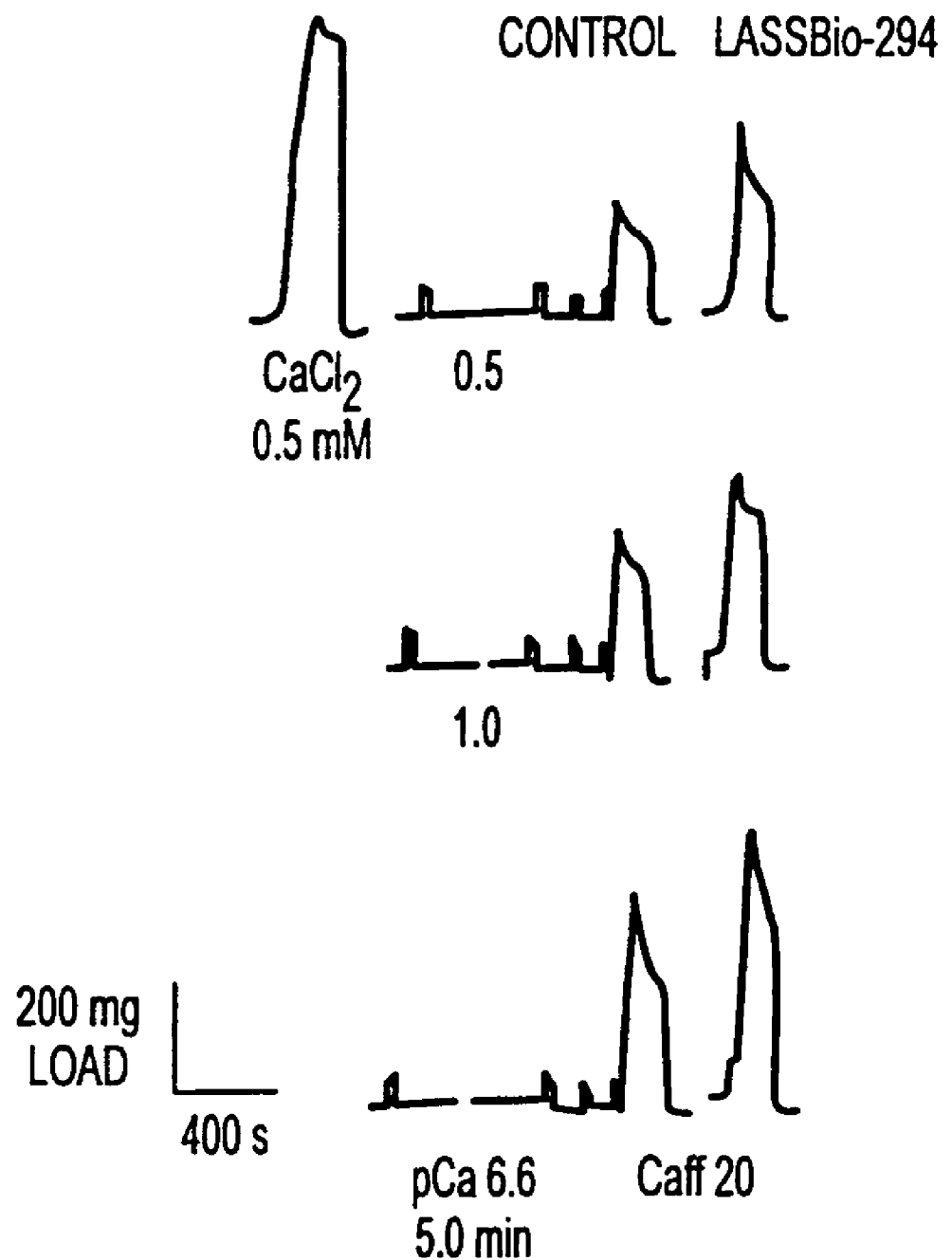
FIG. 7. Bundles of left ventricular fibers were treated with saponin and exposed to 0.5 mM $CaCl_2$ to enable maximal tension development (Po). The contracture initiated by caffeine (20 mM) was measured after treatment of the sarcoplasmic reticulum (SR) with a solution of pCa 6.6 in the absence or presence of LASSBio-294 (100 µM0 for 0.5, 1.0 and 5.0 min. N=6. Calibration: Vertical, 10 mm=20 mg load; Horizontal, 10 mm=40 sec.
Figure 8:
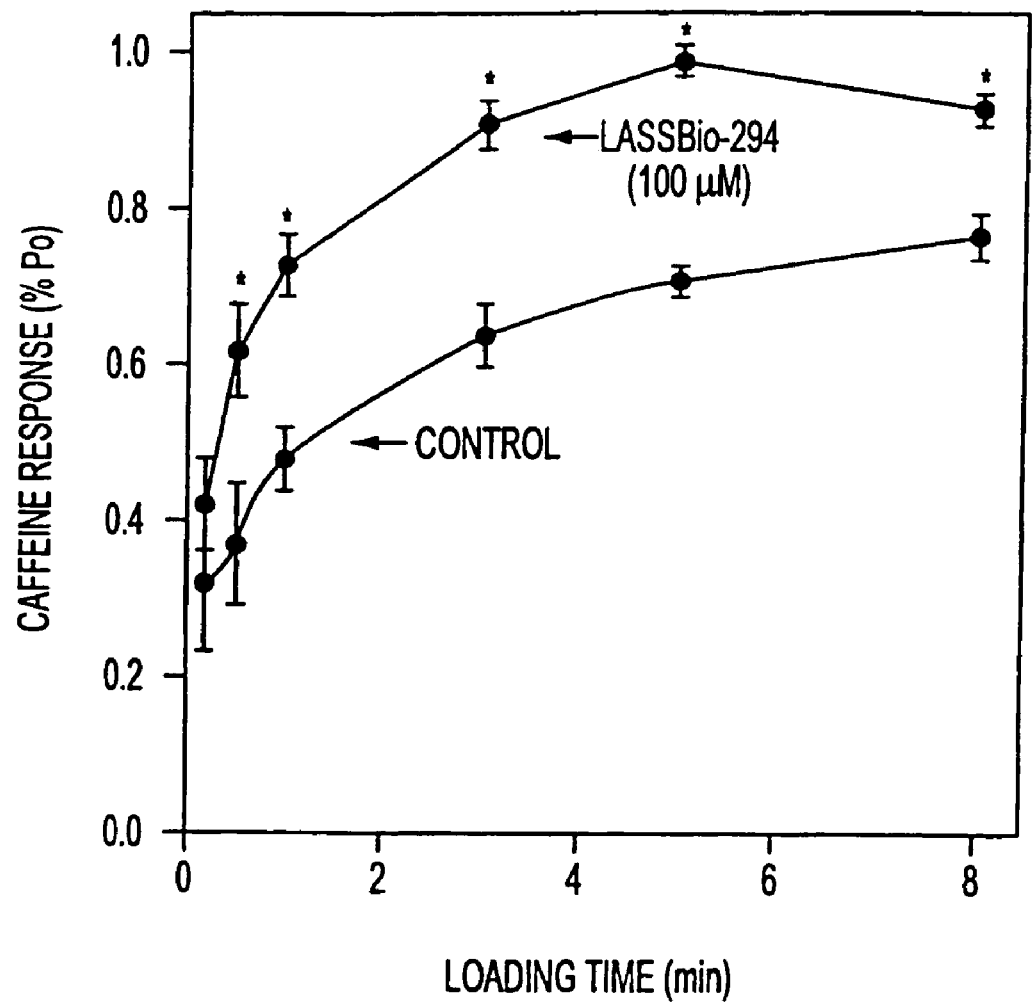
FIG. 8. Contracture induced by caffeine in relation to loading of the sarcoplasmic reticulum with a solution of pCa 6.6.
Figure 9:
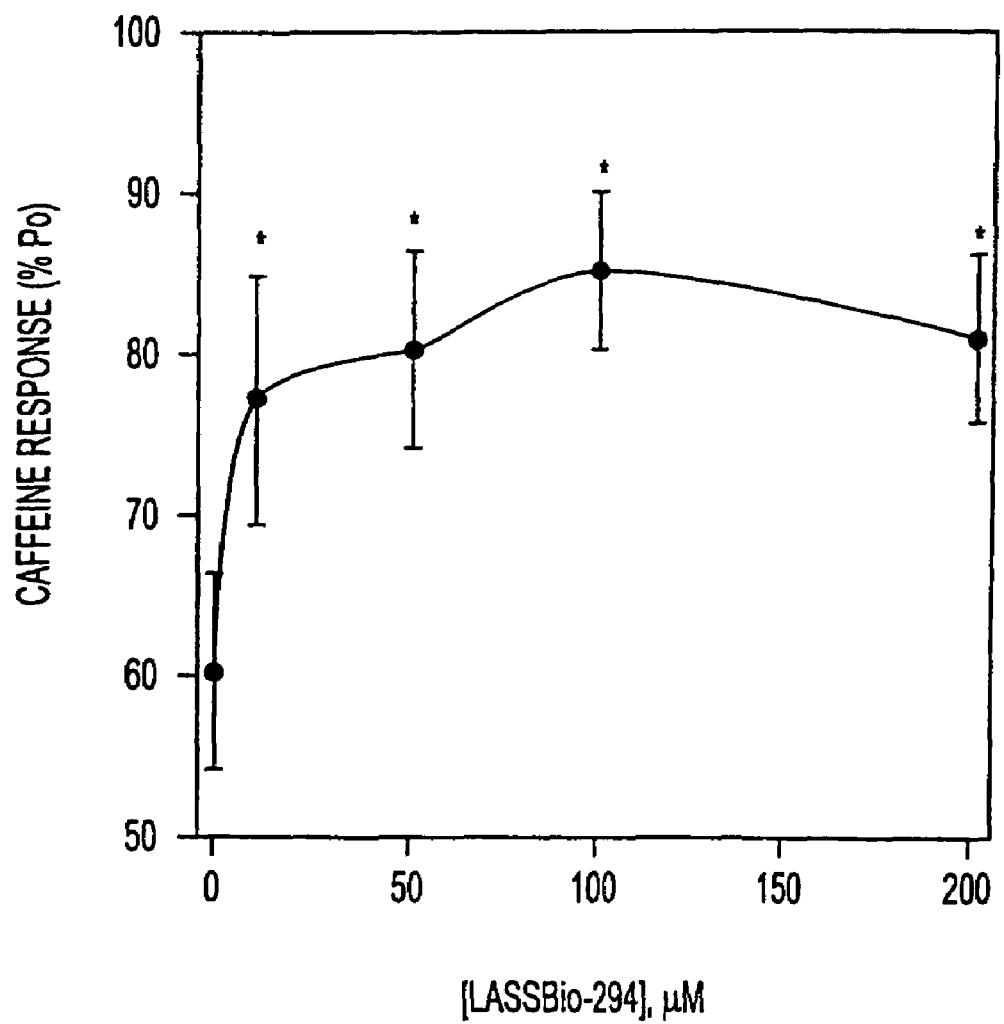
FIG. 9. The contractual responses were obtained during exposure to 20 mM caffeine after loading of the sarcoplasmic reticulum with pCA 6.6 in the absence and the presence of LASSBio-294.
Figure 11:
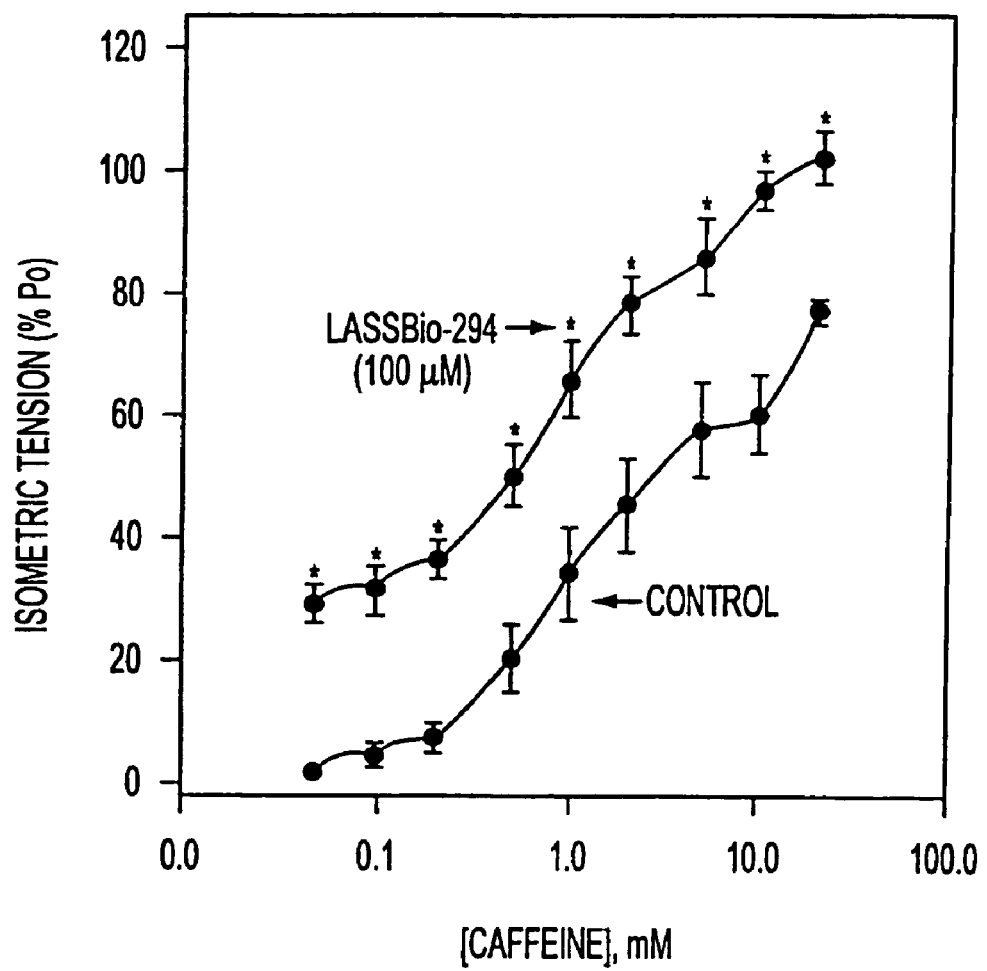
FIG. 11. Concentration-response relationship for contracture induced by caffeine in the presence of 100 µM LASSBio-294. *p<0.01.
Figure 12:
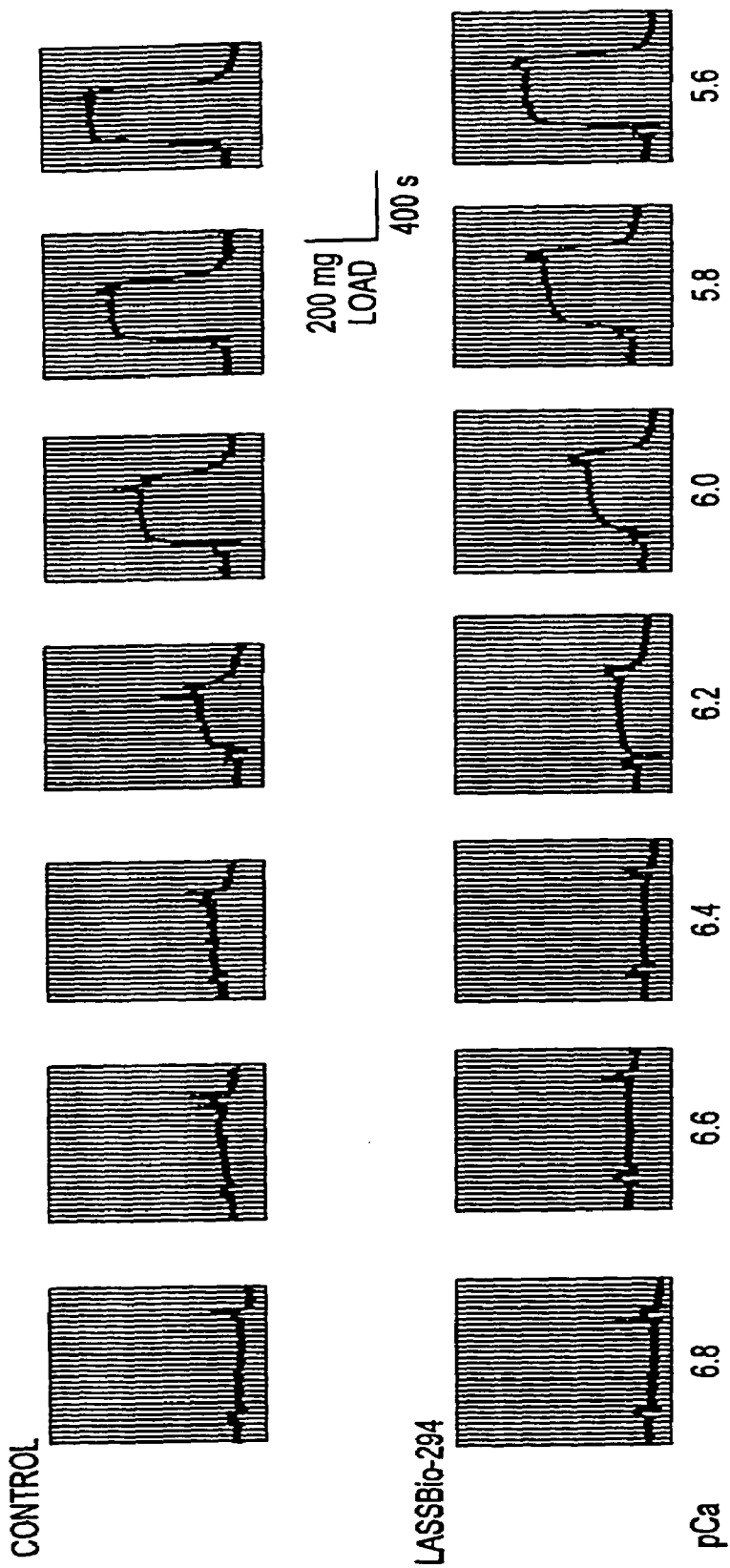
FIG. 12. Muscle bundles were treated with 1% Triton X-100 for 60 min and exposed to solutions containing increasing concentrations of $Ca^{2+}$ in the presence or absence of LASSBio-294 (100 µM). Calibration: Vertical, 10 mm=20 mg; Horizontal, 10 mm=40 sec.
Figure 13:
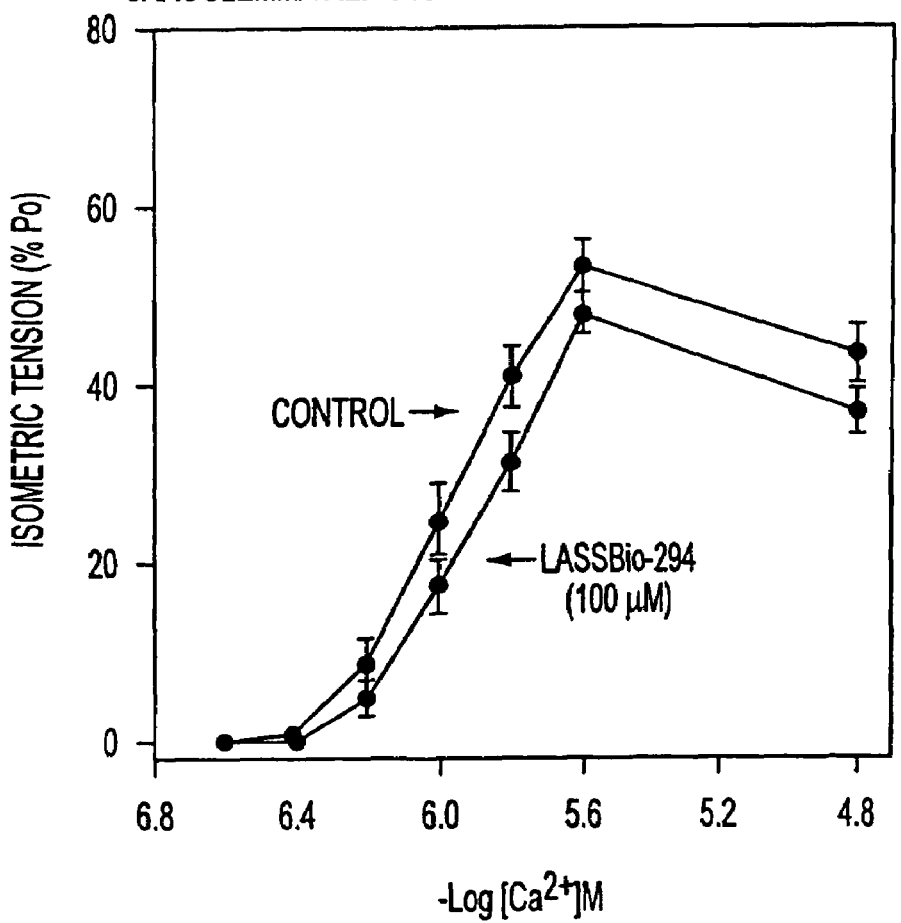
FIG. 13. Bundles of left ventricular muscles were treated with Triton X-100 and exposed to increasing concentrations of $Ca^{2+}$. Muscle tension expressed as % of the maximal response induced by 0.5 mM $CaCl_2$ is graphed as a function of pCa.

Isolated Cardiac Muscle a FIG. 7 illustrates a test that demonstrates increased uptake of Ca$^{2+}$ by the sarcoplasmic reticulum (SR) of LASSBio-294 treated fibers after caffeine induced contraction.

b. Graphic representation of the tests in FIG. 7 showing the effect of LASSBio-294 on uptake of Ca$^{2+}$ by sarcoplasmic reticulum in isolated cardiac muscle with sarcolemma removed. Uptake follows contracture induced by caffeine measured as a function of loading time, shown in FIG. 8.

c. FIG. 9 illustrates the effect of LASSBio-294 on tension in isolated cardiac muscle with sarcolemma removed was measured. Measurement of contraction induced by caffeine, as a function concentration of LASSBio-294 in bathing solution. FIG. 9 is a graphic representation of the effect of increasing concentrations of LASSBio-294 between 0 and 20 μM. Response to caffeine increases until 10 μM LASSBio-294 level.

d. This test demonstrates the effect of increasing concentrations of caffeine from 0.05 to 10 mM on contractile tension. FIG. 10 shows data comparing control to 100 μM LASSBio-294.

e. FIG. 11 shows a graphic representation of data in FIG. 10 showing isometric tension elicited by caffeine. Contraction of LASSBio-294 treated fibers is increased over control at all concentrations.

f. FIG. 12 illustrates the effect of LASSBio-294 on sensitivity of cardiac fibers to calcium. Calcium levels can induce isometric twitch. At each level of pCa the isometric twitch response of fibers was greater in the presence of LASSBio-294 than in control.

g. FIG. 13 provides a graphic representation of data in FIG. 12.

General Method

Bundles of left ventricular muscle (130 μm diameter and 1–2 mm in thickness) from Wistar rats were dissected out and mounted for measurement of isometric tension. The muscles were treated with saponin solution (0.5%) for 5 minutes to block the permeability of the sarcolemma. The membranes of the SR were then fixed with Triton X-100 (1% v/v) with the objective of investigating the effects of LASSBio-294 on the sensitivity of the contractile system Ca$^{2+}$. The treatment does not interfere with the maximal tension developed by cardiac muscle induced by CaCl$_2$ (0.05). Caffeine is used to elicit contraction in muscle. Comparison of caffeine alone to caffeine in the presence of LASSBio-294 was measured.

Example 6

Isolated Human skeletal muscle

Figure 14:
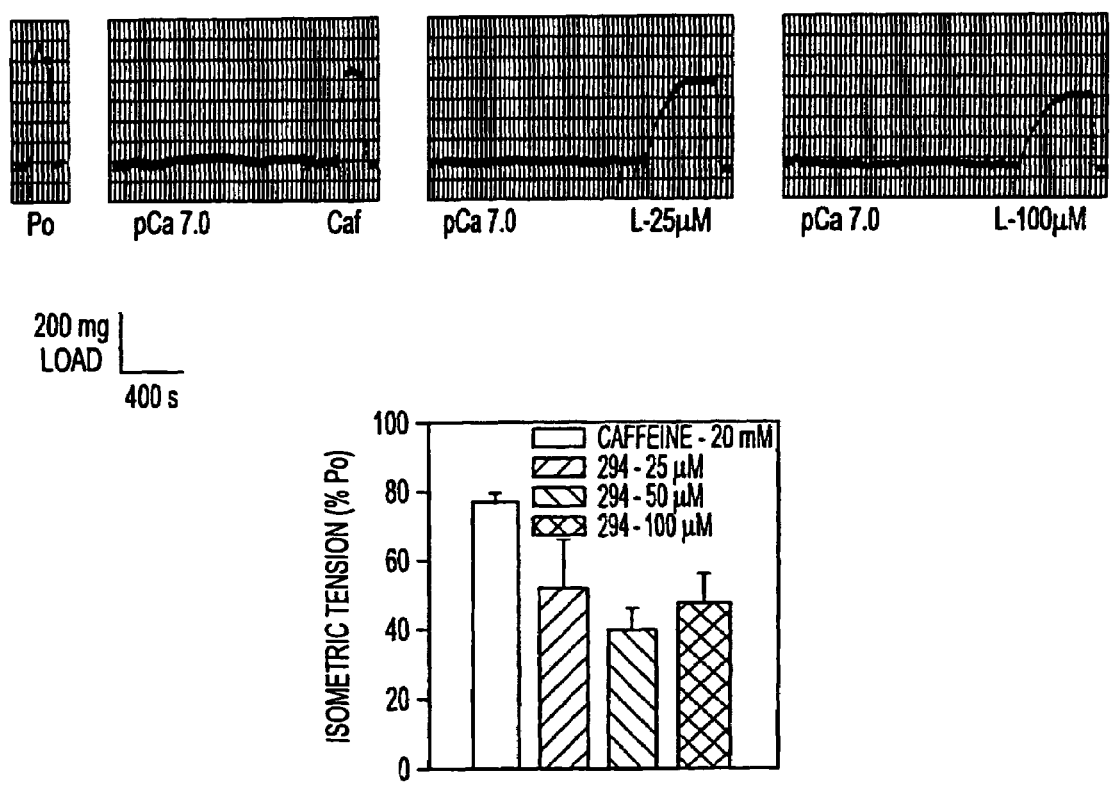
FIG. 14. Isolated human skeletal muscle fiber from the vastus lateralis (sarcolemmal membrane-free) was exposed to 0.5 mM of $CaCl_2$ to enable maximal muscle tension (Po). The histogram show the effect of LASSBio-294 at concentrations of 25, 50 and 100 µM on induced tension in human fibers. N=6 Calibration: Vertical; 10 mm=20 mg; Horizontal, 10 mm=40 s.

FIG. 14 illustrates that LASSBio-294 induces the release of Ca$^{2+}$ from the sarcoplasmic reticulum of isolated human skeletal muscle fibers with sarcolemmal membrane removed. The histogram shows effect of LASSBio-294 at concentrations of 25 μM, 50 μM, and 100 μM on induced tension in human muscle fibers.

General method

Isolated muscle fiber from the vastus lateralis was exposed to 0.5 mM of CaCl$_2$ to enable maximal muscle tension. The contractile response to caffeine was observed after loading of the sarcoplasmic reticulum (SR) with a solution of pCa of 7.0 for 3 min., LASSBio-294 evoked a contraction in the human by liberating Ca$^{2+}$ from the SR.

Example 7

Figure 15:
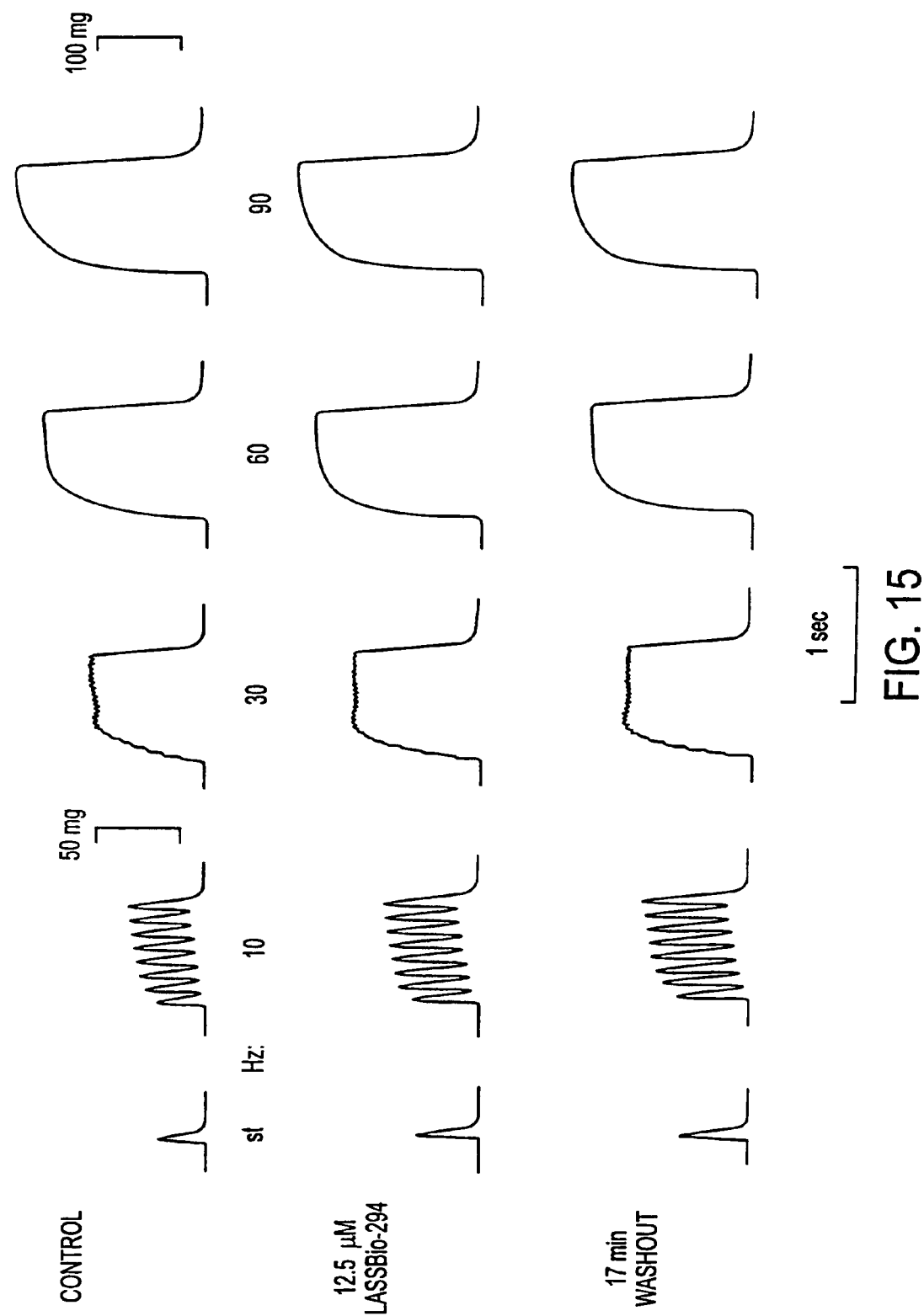
FIG. 15. Effect of 12.5 µM of compound 294 on force development in a single muscle fiber stimulated at different frequencies. The frequency of stimulation in Hz is indicated under each trace. Top panel, stimulating cycle done in Ringer without compound 294. Middle panel, stimulating cycle done 17 min after the fiber was bathed with compound 294. Bottom panel, second cycle of stimulation done 17 min after compound 294 was washed out with Ringer. Force calibration bars are 50 mg for twitches and 10 Hz simulations and 100 mg for 30, 60, and 90 Hz.
Figure 16:
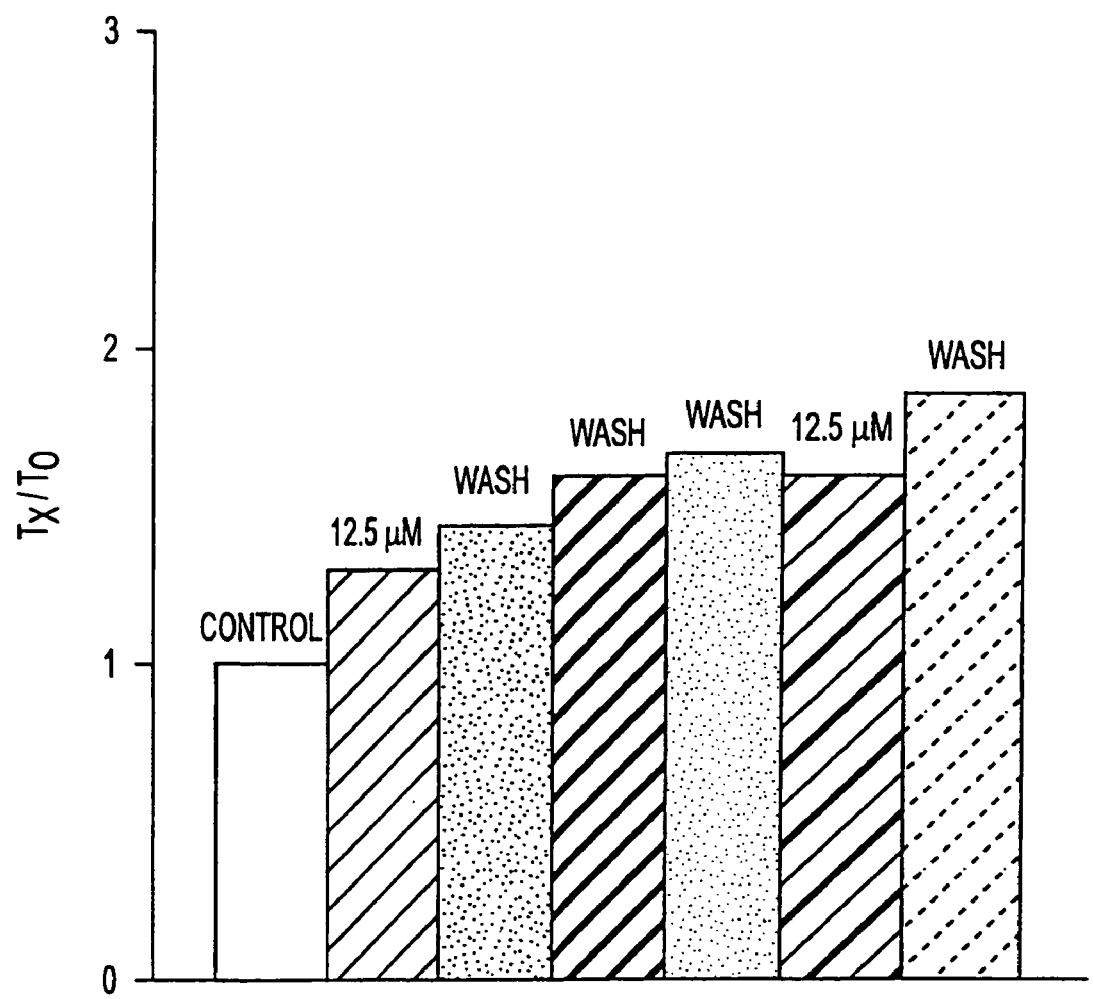
FIG. 16. Histogram showing the effect of 12.5 µM compound 294 and after washing out LASSBio-294 on fractional twitch tension $(T_x/T_o)$. $T_x$ represents the twitch tension obtained when the fiber was bathed with the solutions indicated above each column. The order of the columns are the order in which the simulating cycles were performed.
Figure 17:
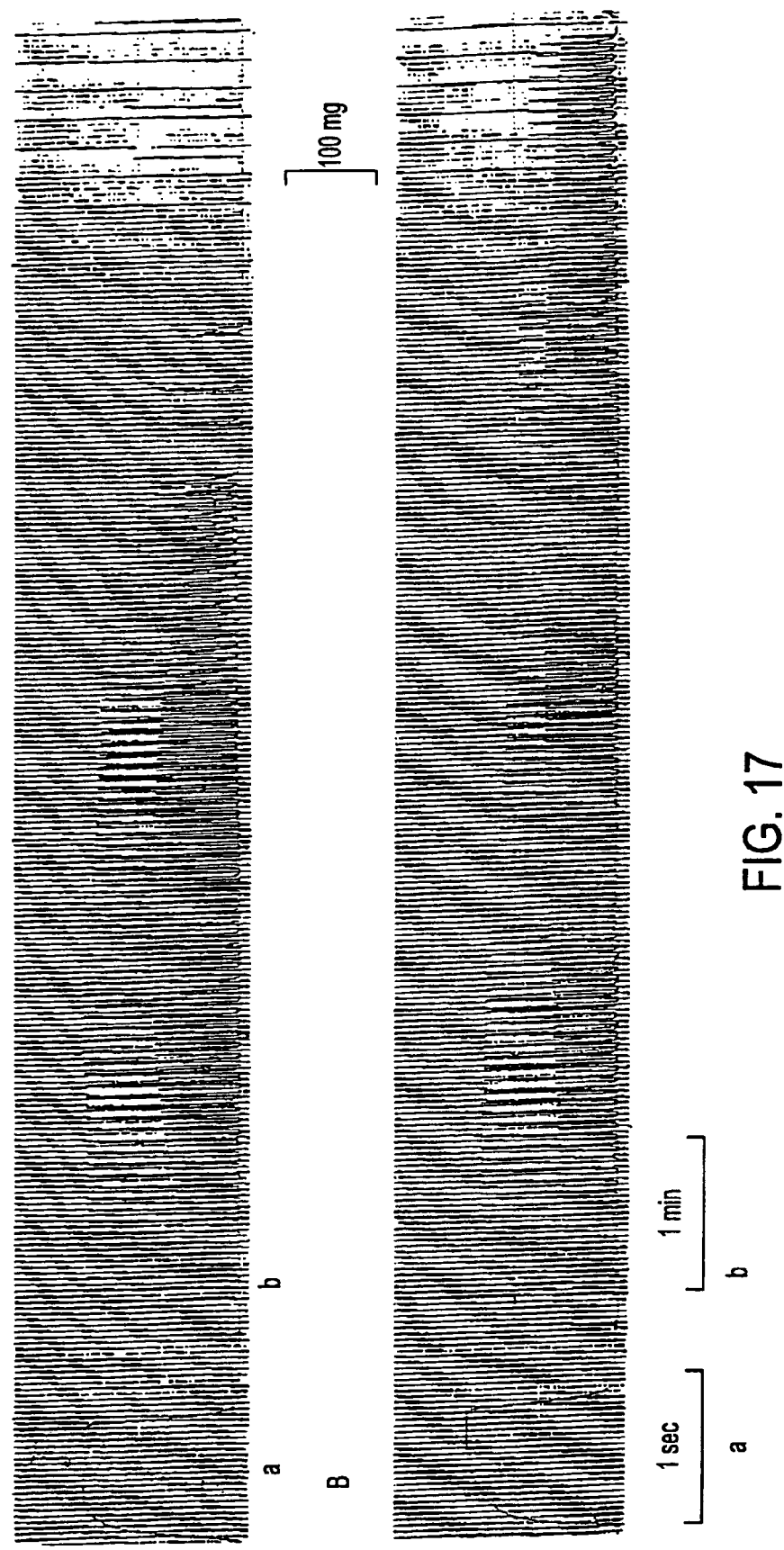
FIG. 17. Time course of fatigue development. Fatigue was produced by 60 Hz, 0.8 sec tetanic stimulations repeated every 4.75 sec with a twitch elicited 2.2 sec after each tetanic stimulation. a) single tetanus. b) repeated tetanic stimulations. Notice the time calibration. A) In 50 µM of DMSO only B) Same as in A, but the fiber was bathed with 50 µM of compound LASSBio-294.
Figure 18:
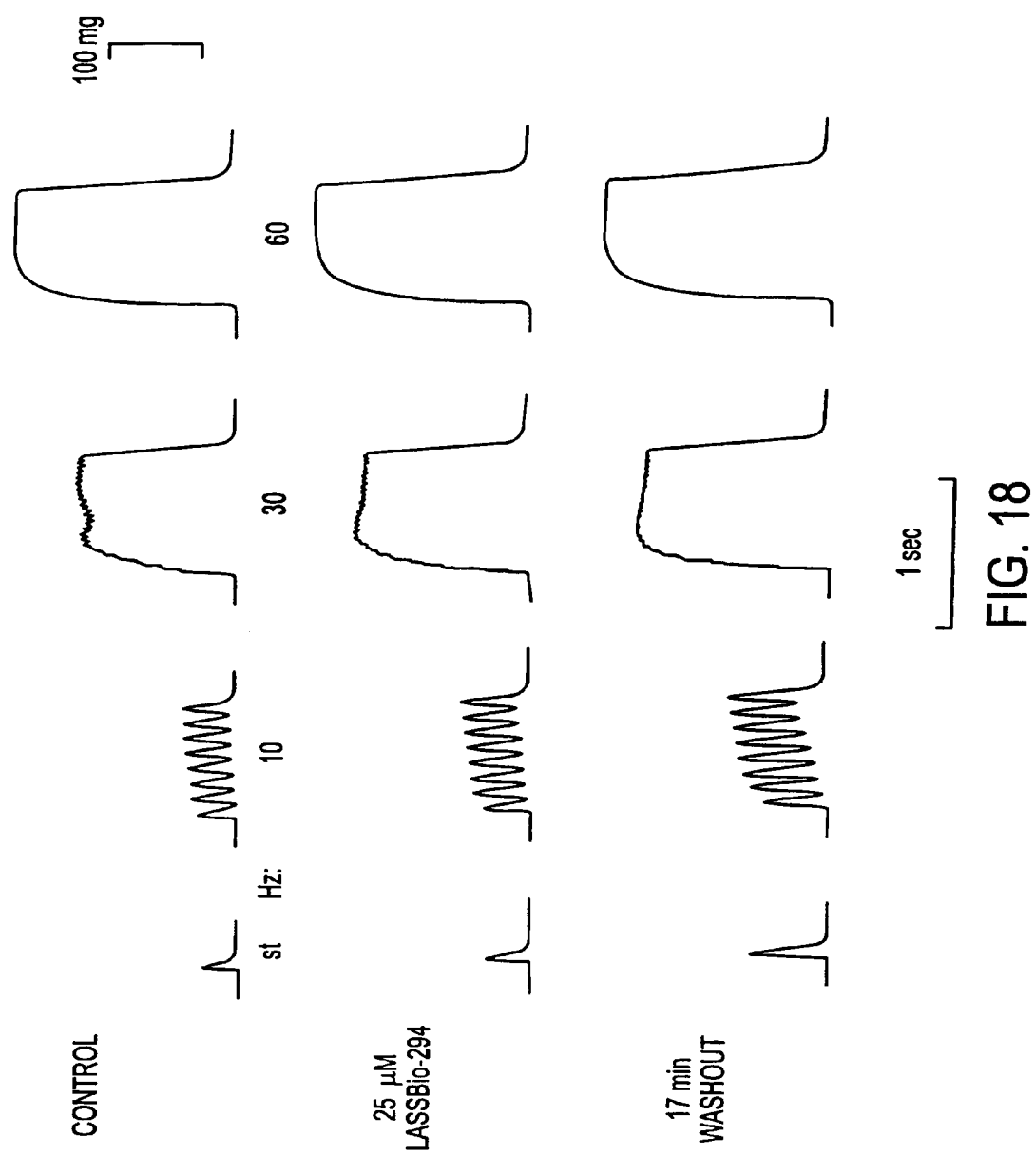
FIG. 18. Same as FIG. 17, but with 25 µM of LASSBio-294. The force calibration bar is the same for all the stimulation frequencies.
Figure 19:
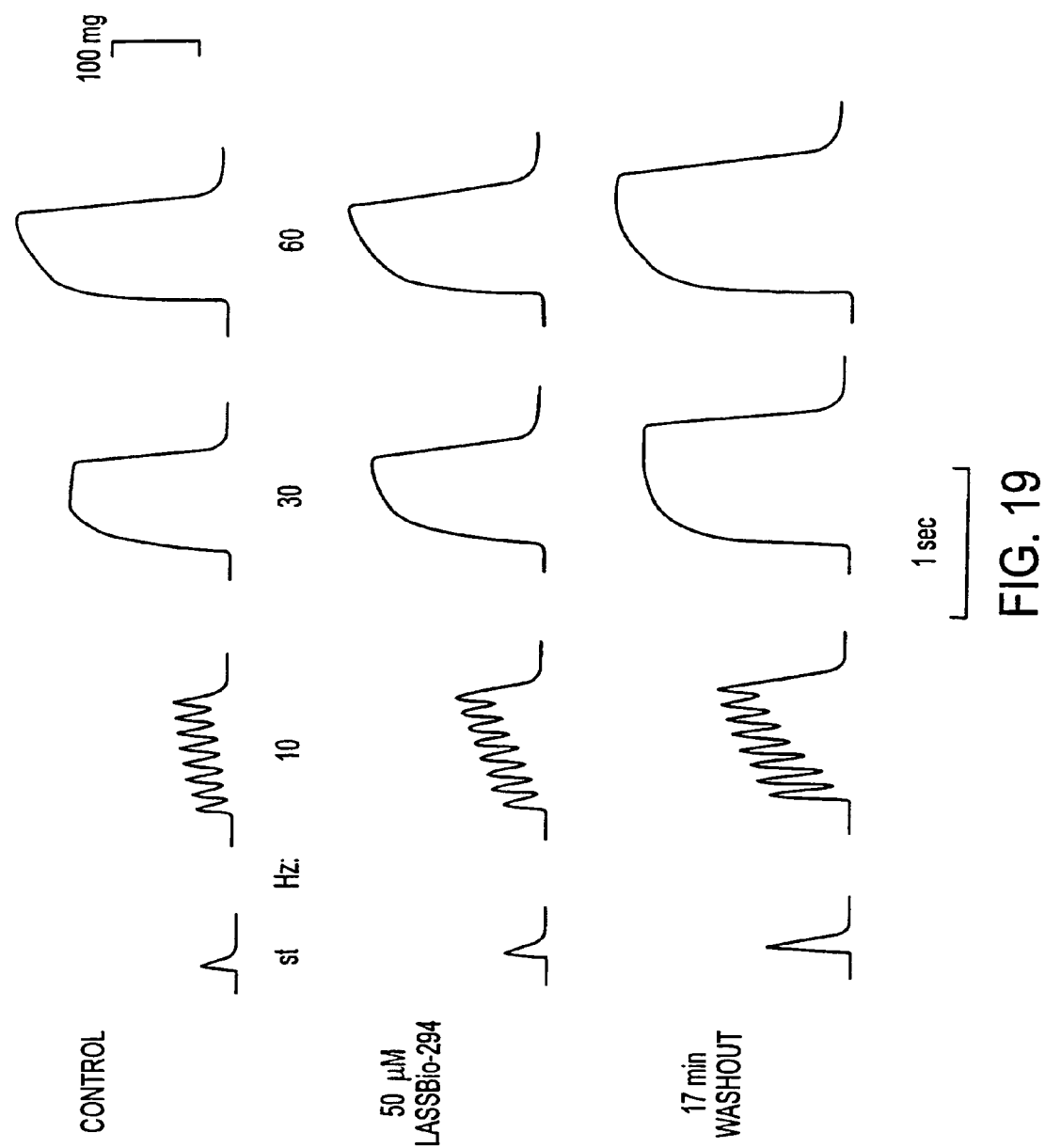
FIG. 19. Same as FIG. 17, but with 50 µM of LASSBio-294. The force calibration bar is the same for all the stimulation frequencies.
Figure 20:
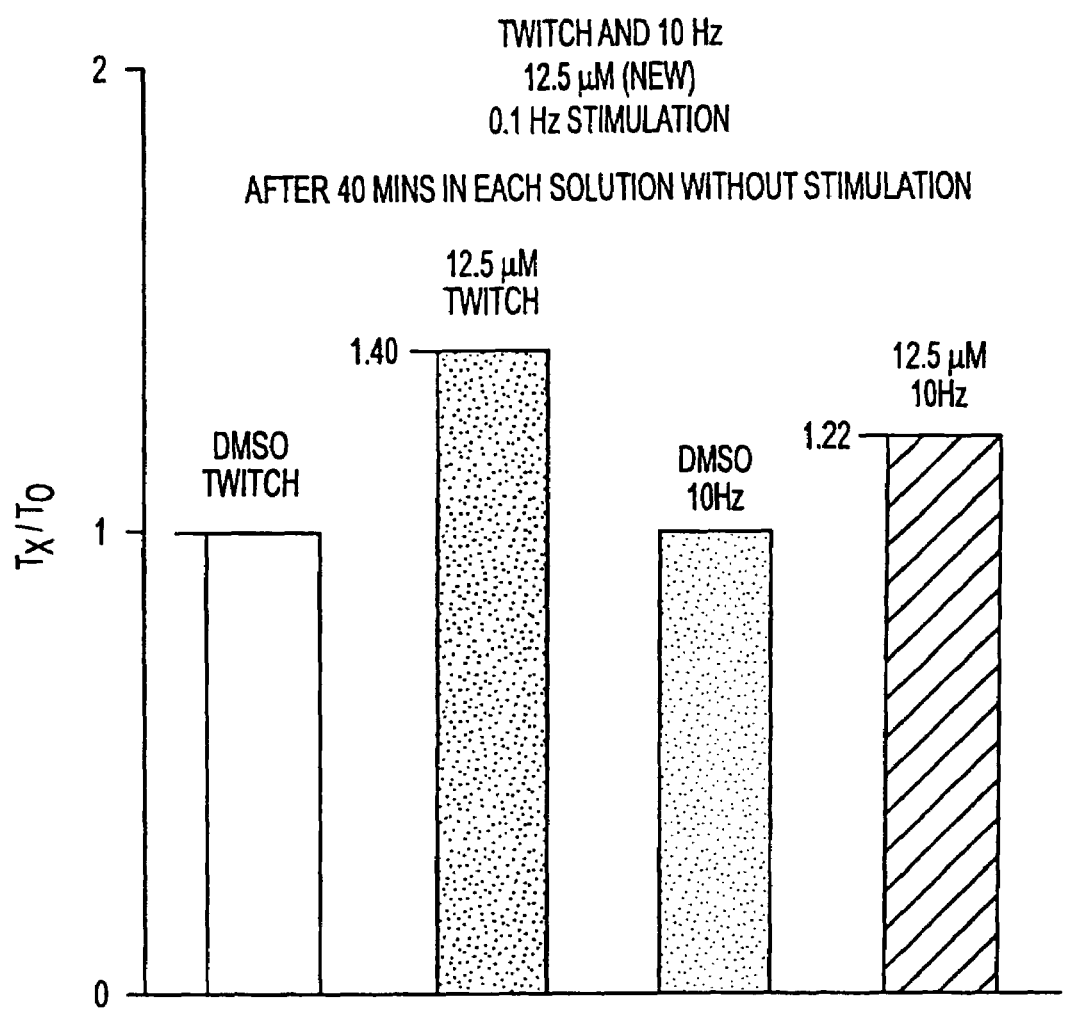
FIG. 20. Effect of 12.5 µM LASSBio-294 on peak twitch tension and maximal 10 Hz tetanic tension. The measurements were taken after the fibers had been in each solution for 40 min without being stimulated. Each column represents the ratio of the corresponding tension $(T_x)$ divided by the corresponding control tension $(T_o)$ which was taken as 1.
Figure 21A:
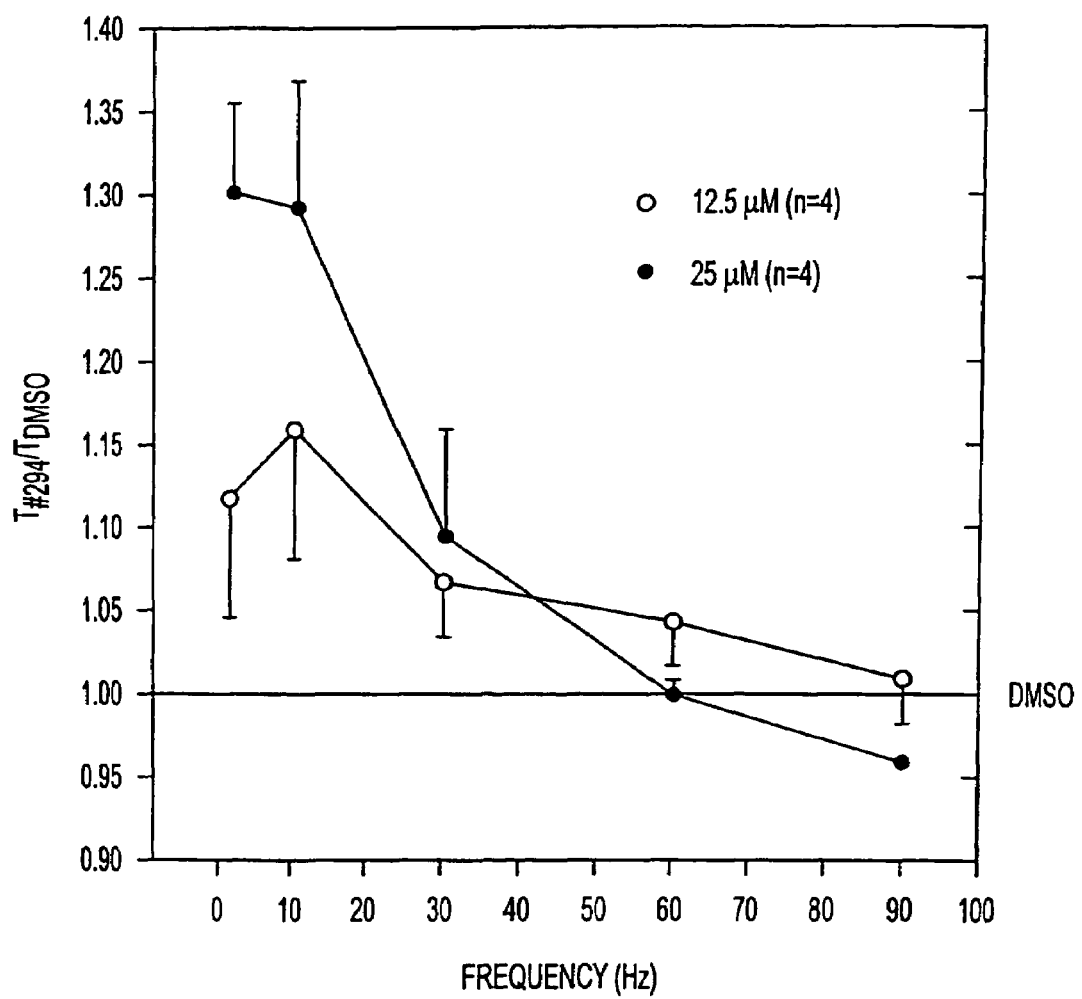
FIG. 21A. Effect of 12.5 (circles) and 25 (dots) µM of LASSBio-294 on fractional tension potentiation at different frequencies of stimulation. Fractional tension is expressed as the ratio of the maximal force obtained at each different frequency (T#294) divided by the maximal force obtained in Ringer plus DMSO at each corresponding different frequency $(T_{DMSO})$.
Figure 21B:
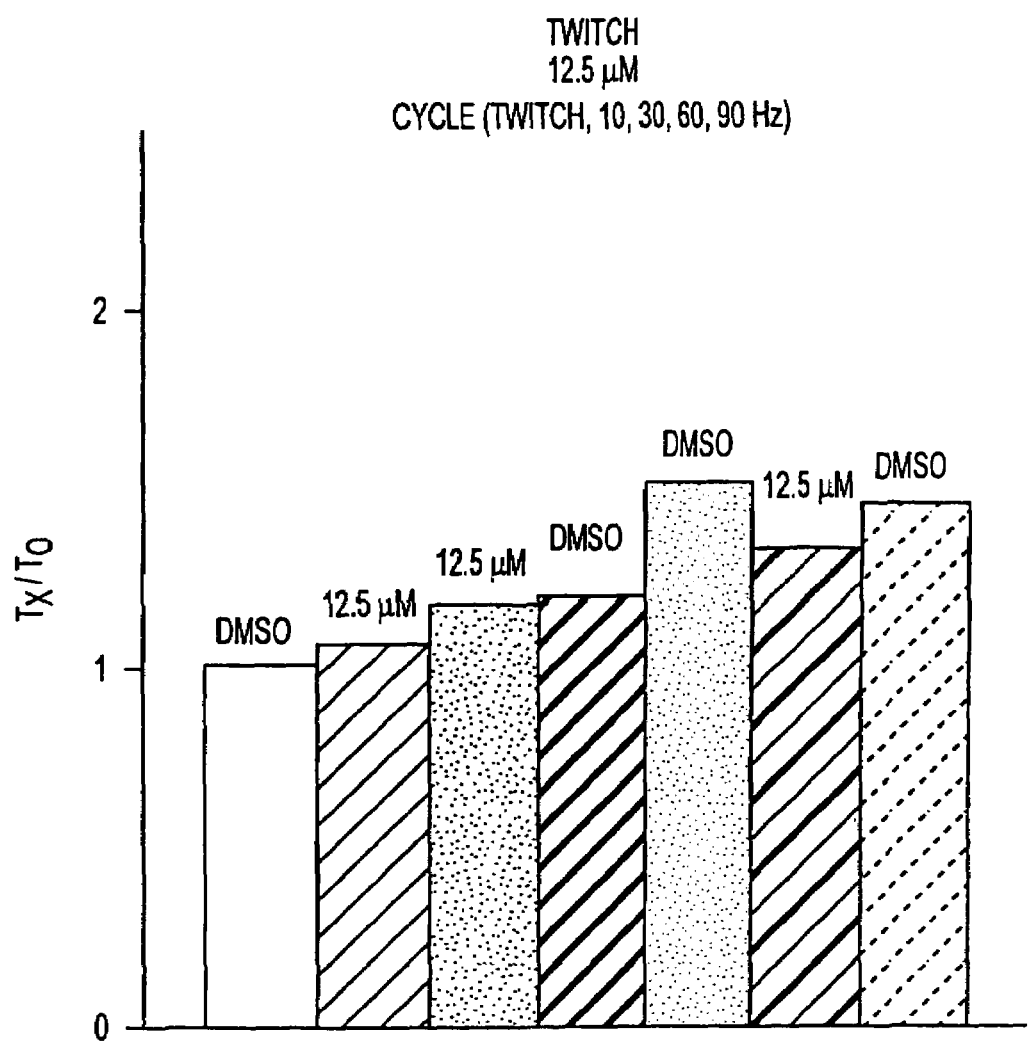
FIG. 21B. Histogram showing the effect of 12.5 µM LASSBio-294 and wash out of the compound on twitch tension ratio (Tx/To). Twitch tension obtained during the first cycle of stimulation in Ringer and DMSO was taken as one (To). Tx represents the twitch tension obtained when the fiber was bathed with the solutions indicated above each column. The order of the columns is the order in which the stimulating cycles were done.
Figure 22:
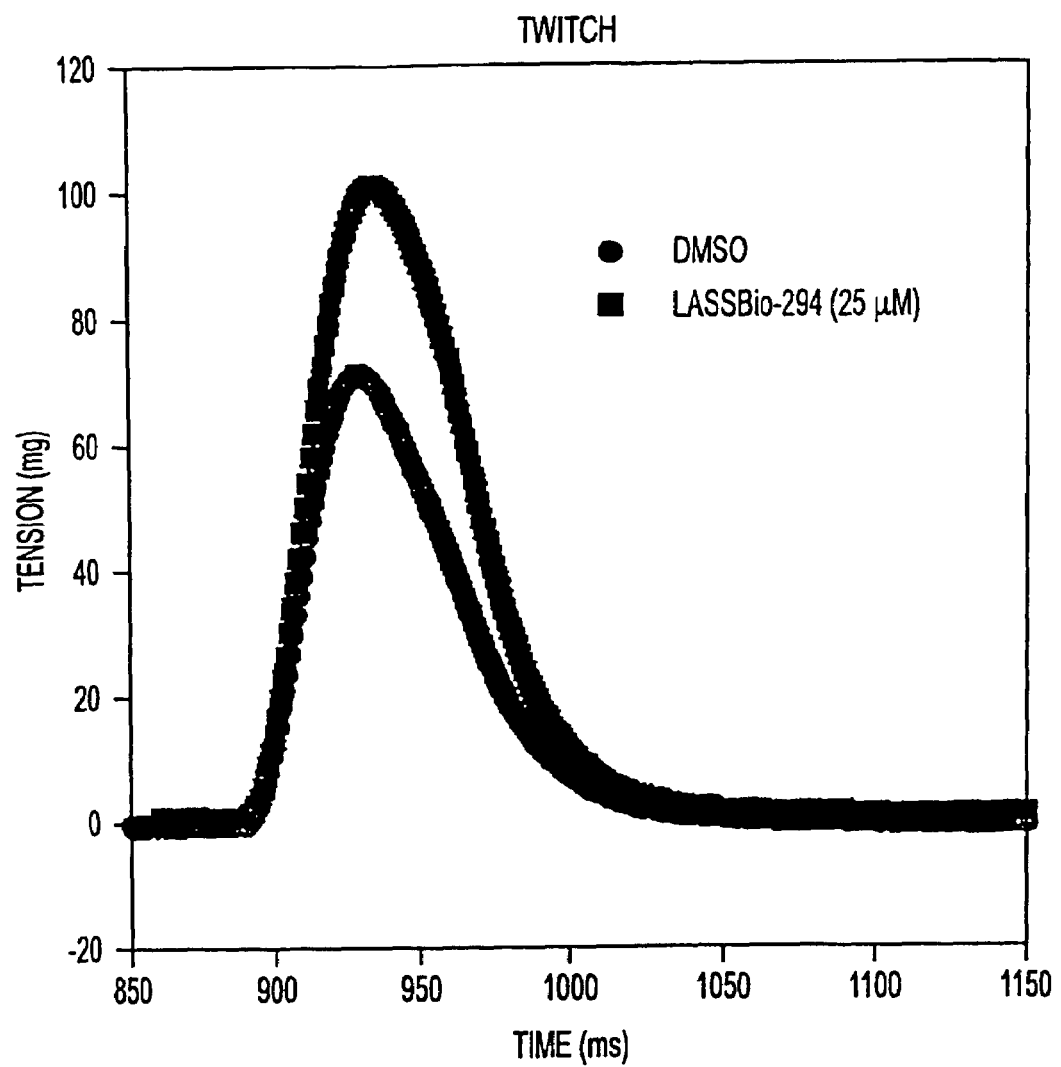
FIG. 22. Comparison of the time course of twitch tension obtained in Ringer plus DMSO (dots) with the time course of twitch tension elicited in Ringer plus 25 µM of LASSBio-294 (squares).
Figure 23:
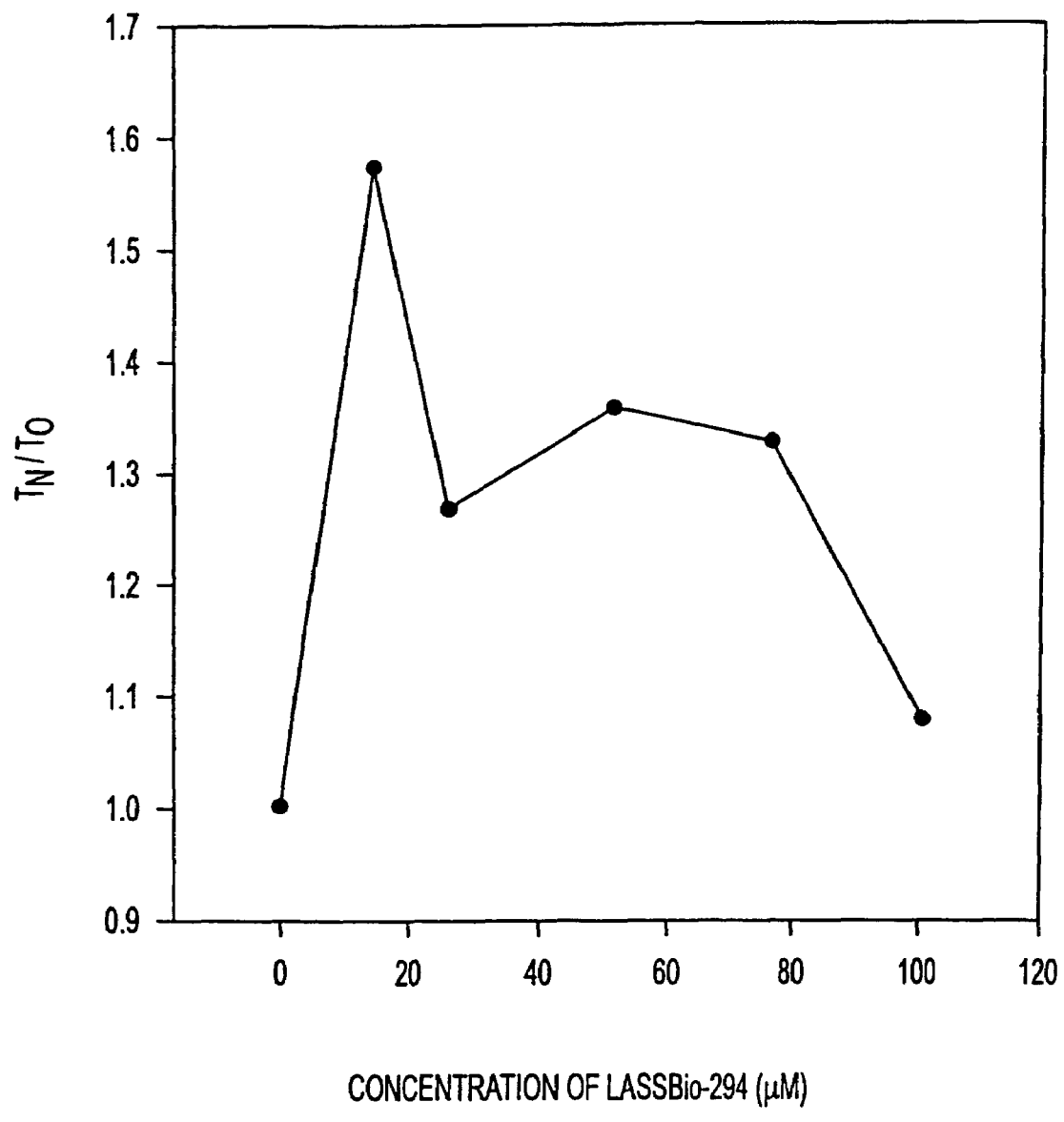
FIG. 23. Relationship between fractional twitch tension and LASSBio-294 concentration. Peak twitch tensions $(T_n)$ were measured during the second stimulation cycle after the cells were in different LASSBio-294 concentrations and ratio against peak twitch tension $(T_o)$ in Ringer without LASSBio-294 which was taken as 1.
Figure 24:
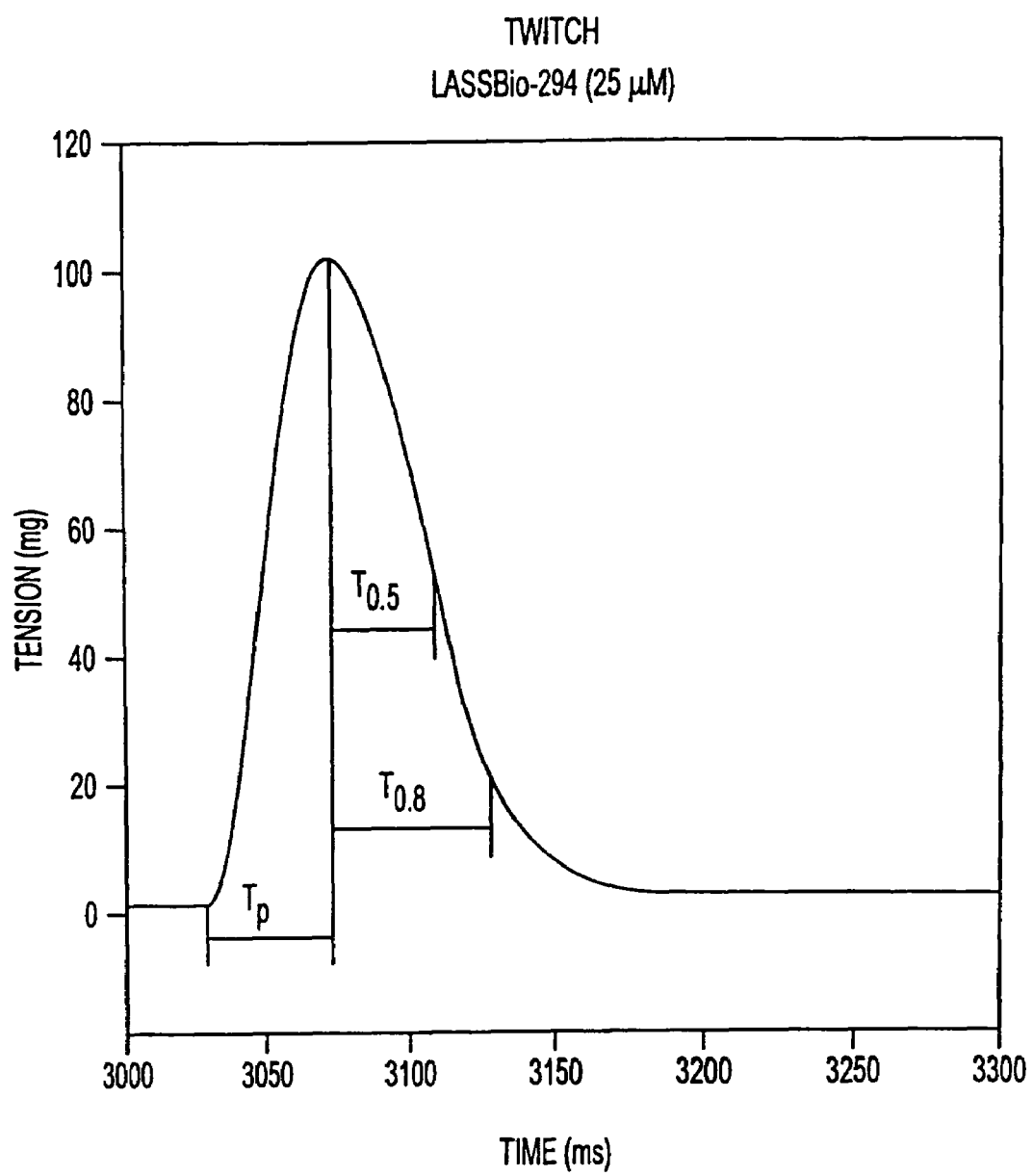
FIG. 24. Time parameters measured during the twitch tension time course. $T_p$ is the time to reach peak force. $T_{0.5}$ is the relaxation time it takes for tension to decline from peak tension to 50% of the peak tension. $T_{0.8}$ is the relaxation time it takes for tension to 80% of the peak tension.
Figure 25:
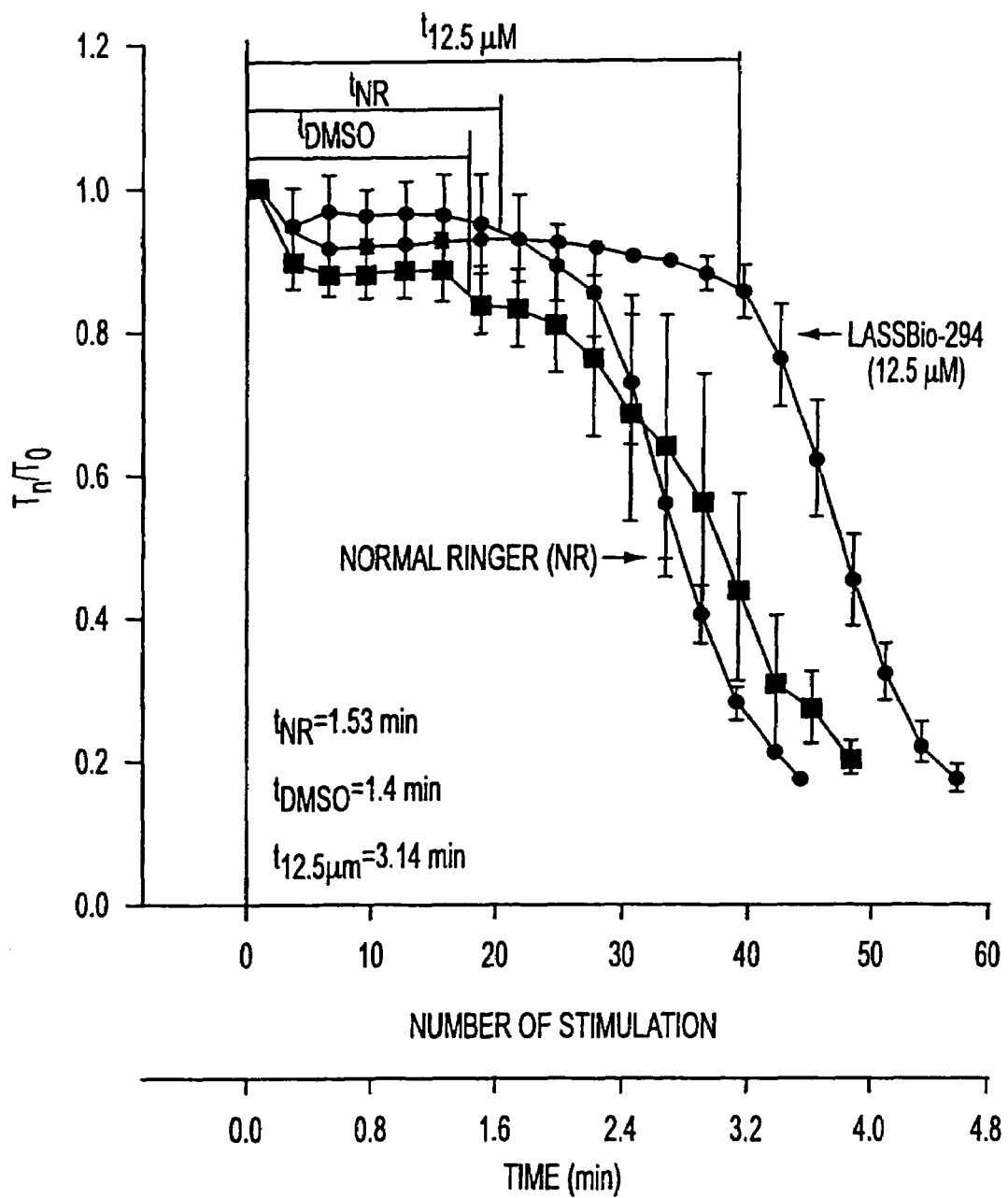
FIG. 25. Effect of LASSBio-294 on the time course of fatigue development. Top trace control experiment, the fiber was bathed with Ringer plus DMSO. Bottom trace, the fiber was bathed with Ringer plus 12.5 µM of LASSBio-294. The fibers were stimulated with the parameters described in methods. In both panels, the first trace is the tension elicited with a 10 Hz stimulation frequency. Force and time calibration bars are 50 mg and 1 sec for the 10 Hz stimulation frequencies and 100 mg and 1 min for the repetitive stimulation.
Figure 26A:
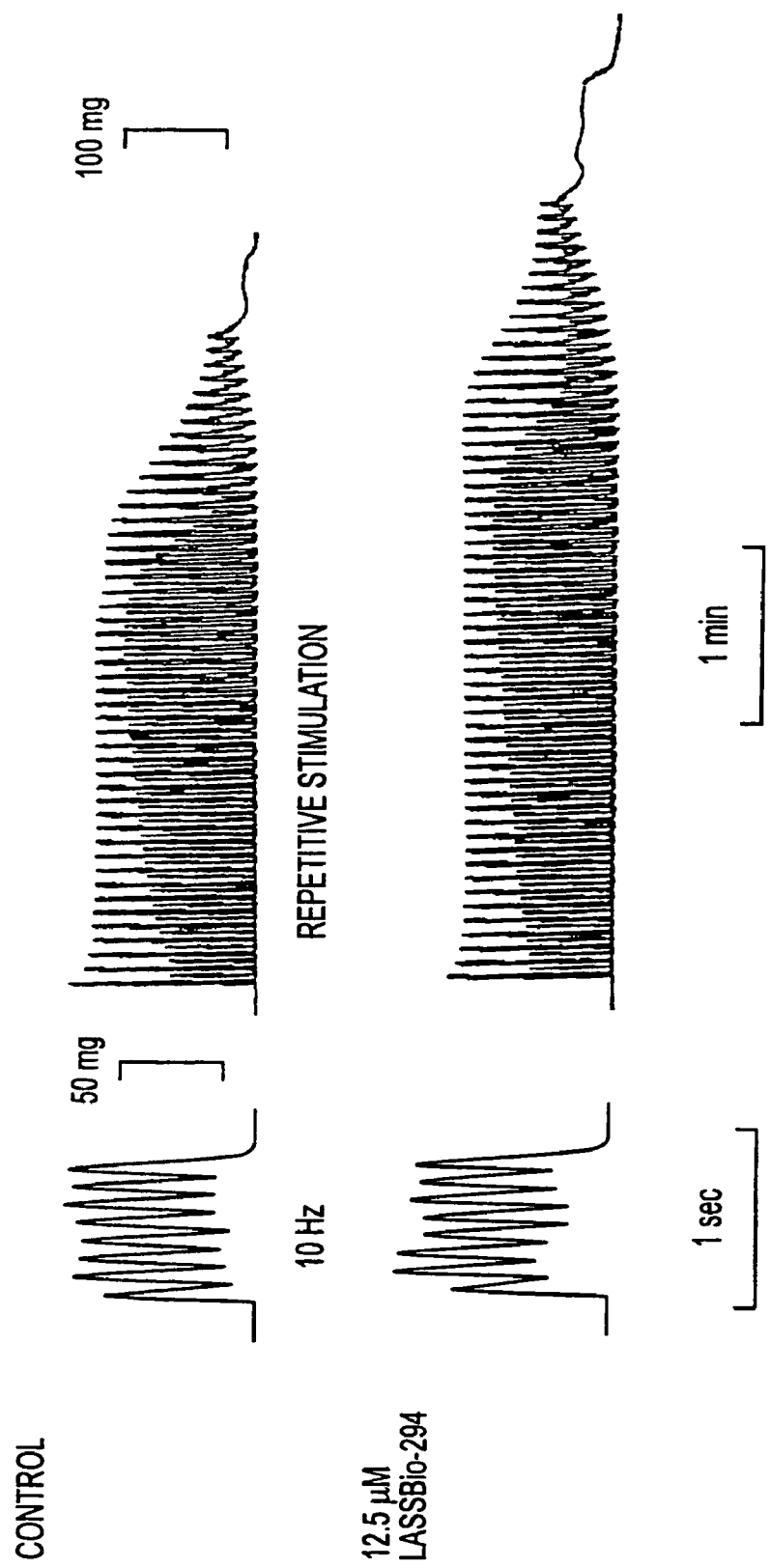
FIG. 26. Summary of the time course of the index of fatigue development elicited in fibers bathed with Ringer only (green dots), Ringer plus DMSO (squares) and Ringer plus 12.5 µM of LASSBio-294 (red dots). $t_{NR}$ $t_{DMSO}$ and $t_{µM}$ indicate the times it takes for tetanic tension to start declining (fatigue) after the beginning of the repetitive stimulation when the fibers were bathed with Ringer only, Ringer plus DMSO and Ringer plus 12.5 µM respectively. Abscissas are expressed either as the number of tetanic stimulations or the time of stimulation.
Figure 26B:
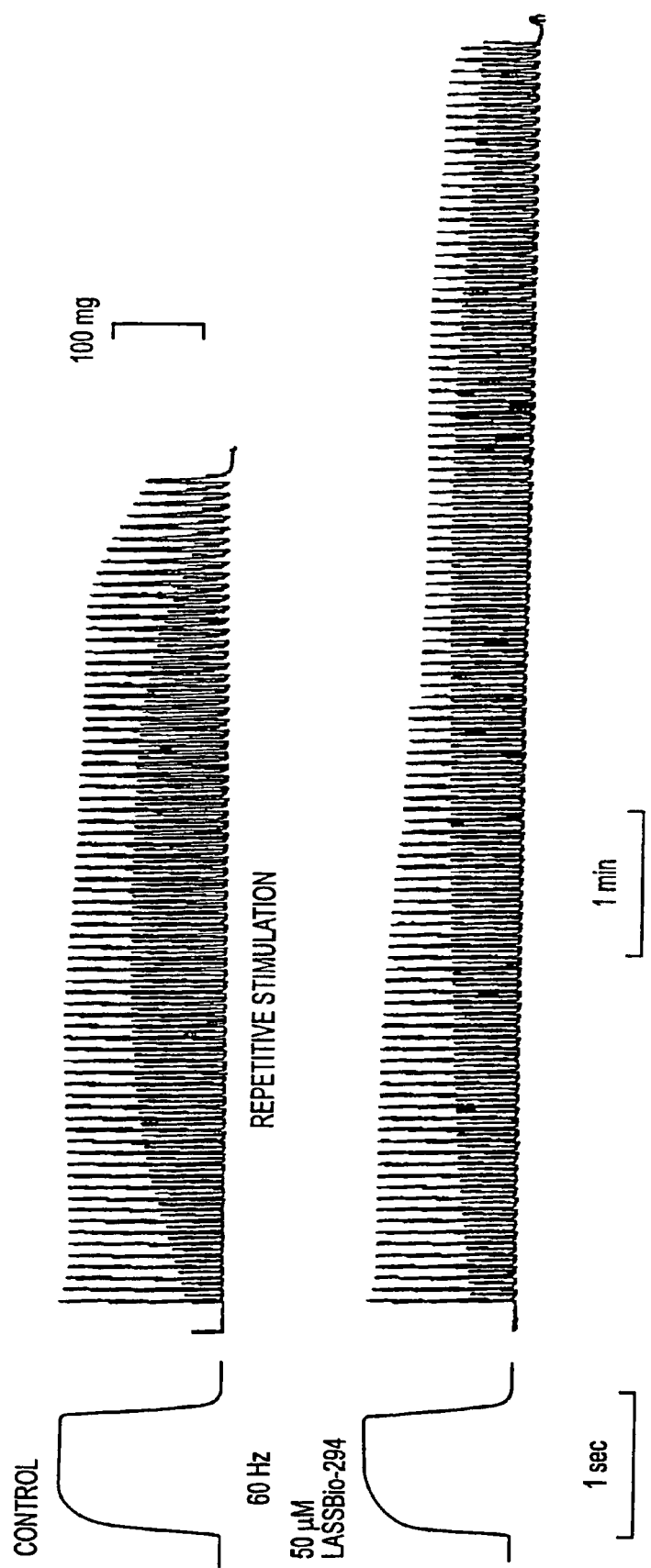
Figure 27:
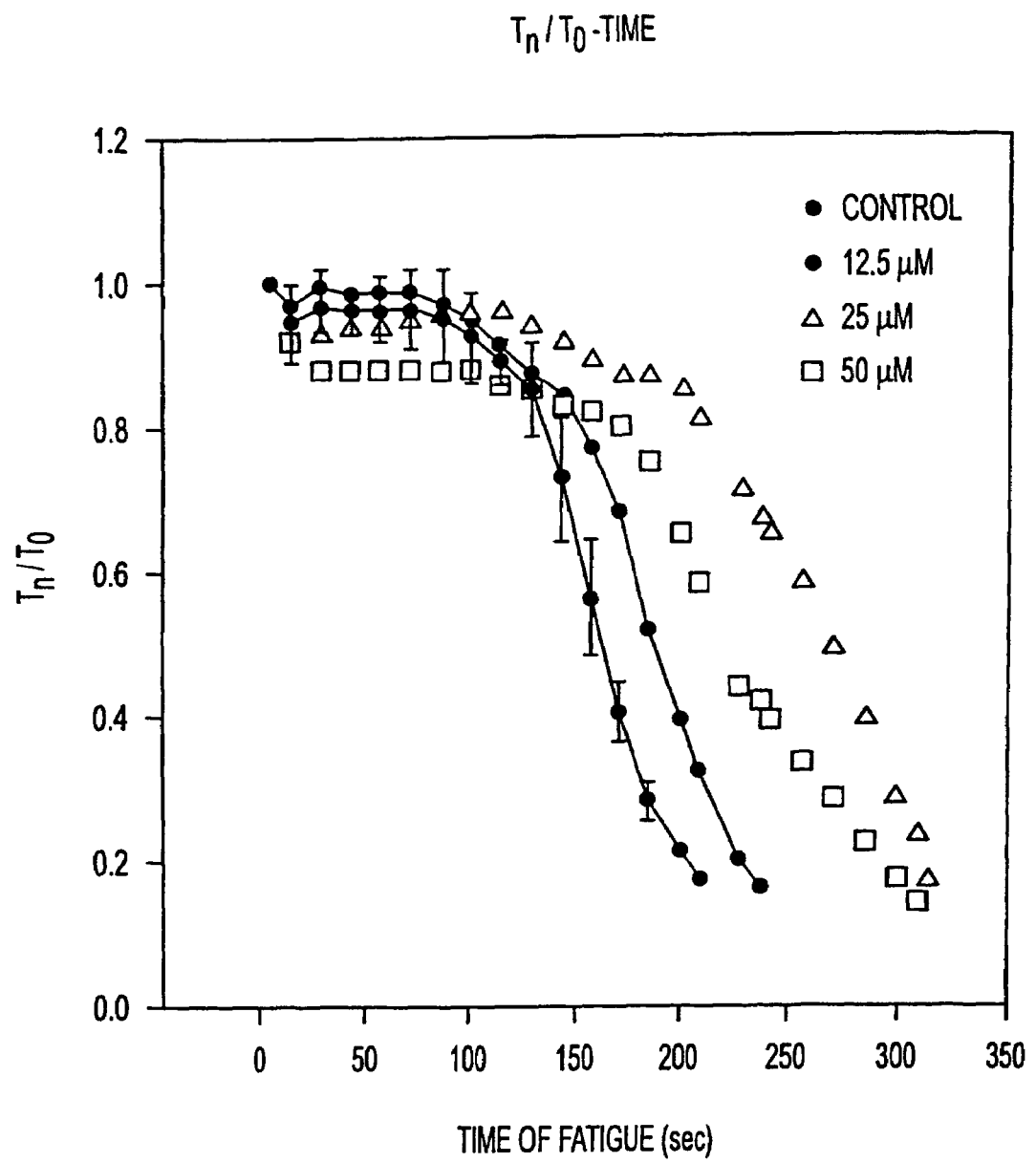
FIG. 27. Time course of the index of fatigue development with different concentrations of compound 294 as indicated. The control curve, done in Ringer only, is the average of three experiments; each of the other correspond to only one fiber.
Figure 28:
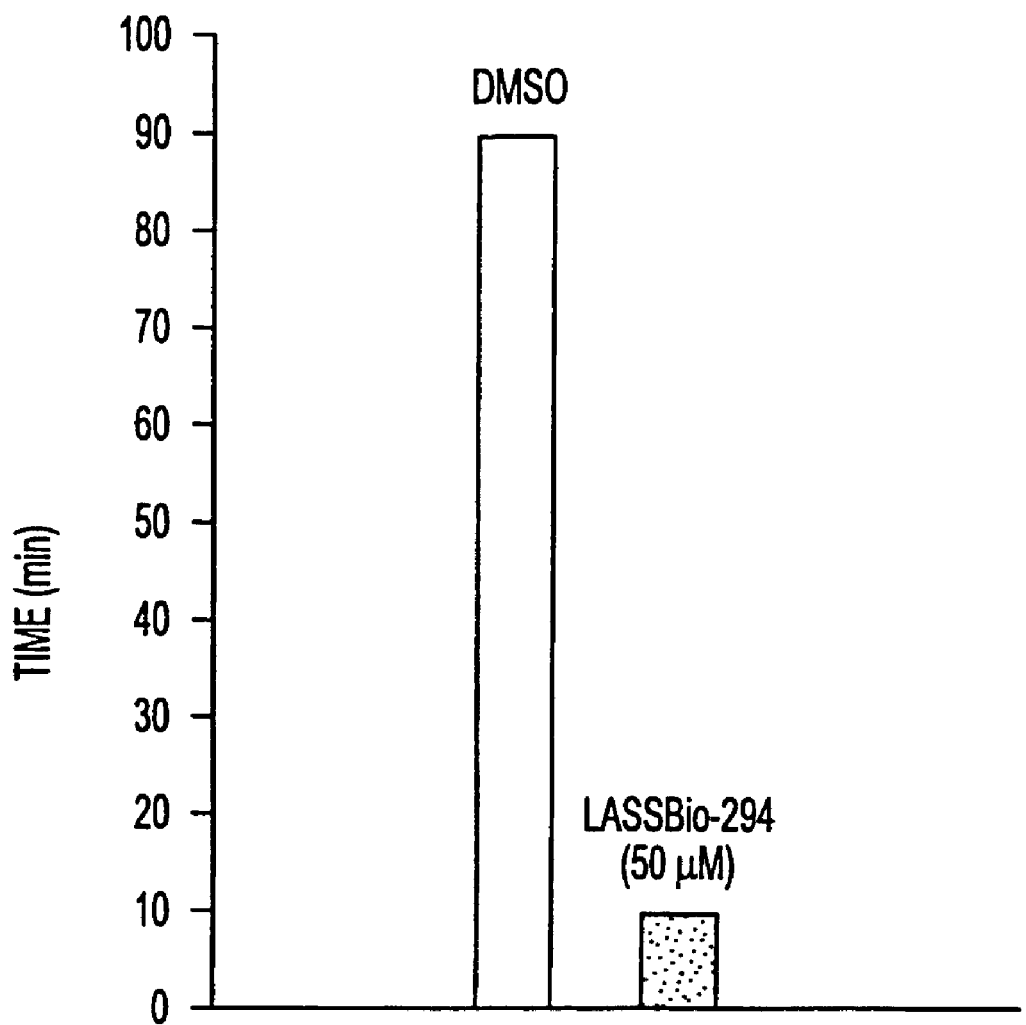
FIG. 28. Time (in min) for tetanic force to decrease (fatigue) to 50% of the original tetanic force during repetitive stimulations as in FIG. 17. Left column in 50 µM of DMSO only (~6 in). Right column in 50 µM of LASSBio-294 (~9 min).
Figure 29:
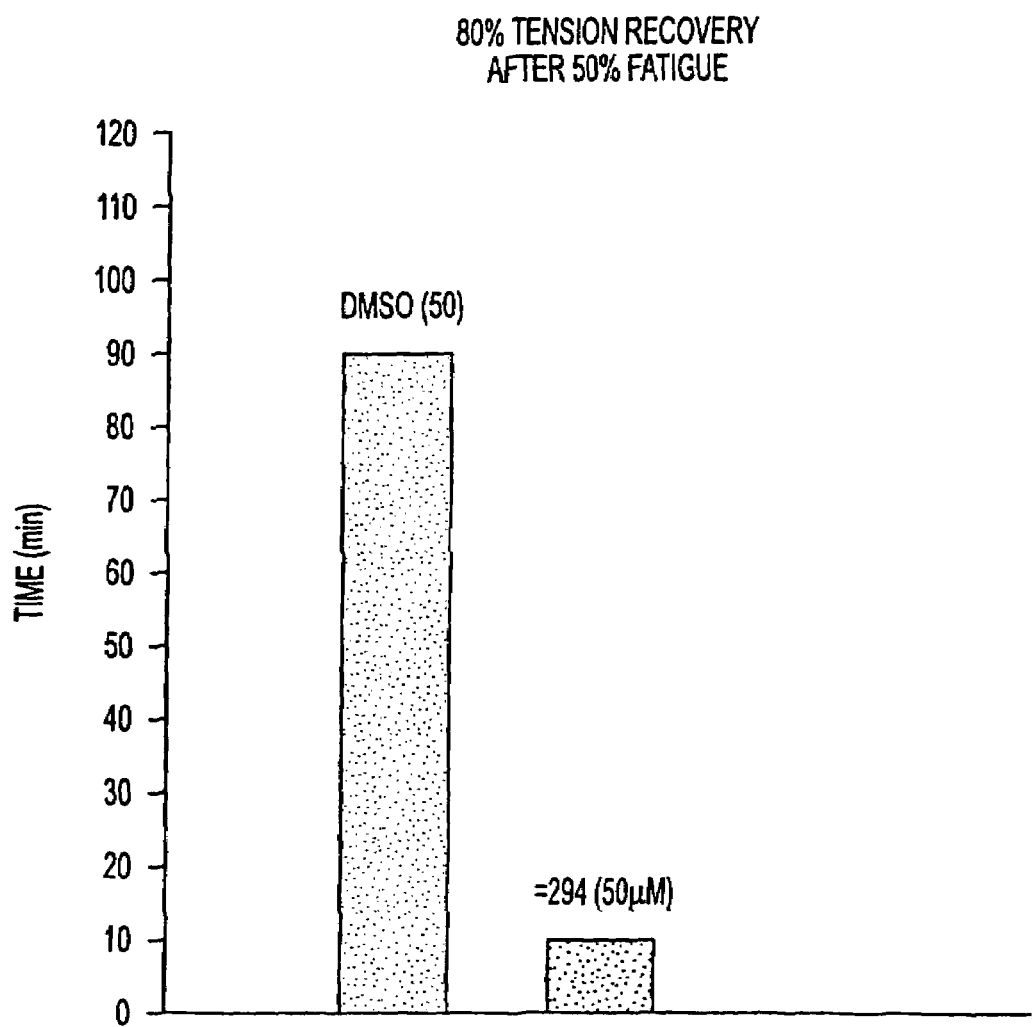
FIG. 29. Time of recovery to 80% of the pre-fatigue tetanic force. Left column in 50 µM of DMSO only (~90 min). Right column in 50 µM of LASSBio-294 (~10 min).

Amphibian Muscle a. FIG. 15 illustrates the measurement of the effect of LASSBio-294 on force development in a single muscle fiber stimulated at different frequencies. Control is Ringer's solution without compound; following is stimulation after wash with plain Ringer's solution.

b. The histogram in FIG. 16 shows effect of 12.5 µM LASSBio-294 on fractional twitch tension with 10 Hz stimulation. $T_x/T_o$ reflects twitch tension after bathing, $T_x$, divided by initial tension in Ringer's solution alone, $T_o$. Bars are labeled and are placed right to left in the histogram, in the order performed.

c. A time course of fatigue development, in FIG. 17, in single muscle fibers comparing 50 uM LASSBio-294 to solvent control demonstrated that fatigue is produced by 60 Hz, 0.8 sec tetanic stimulations, repeated every 4.75 seconds with a twitch elicited every 2.2 sec after tetanic stimulation. A is 50 µM DMSO in Ringer's solution, B is 50 µM LASSBio-294. The time to fatigue in LASSBio-294-treated is approximately 50% longer than control.

d. FIG. 18, same conditions as 7c, with 25 µM of LASSBio-294.

e. FIG. 19, same conditions as 7c, with 50 µM of LASSBio-294.

f. FIG. 20 is a histogram of $T_x/T_o$, 12.5 uM LASSBio-294 compared to DMSO.

g. FIG. 21A shows the effect of two different doses of LASSBio-294 on fractional tension potentiation. FIG. 21A.

h. FIG. 21B shows a histogram effect of 12.5 µM LASSBio-294 on twitch tension ratio, at 10 Hz, 30 Hz, 60 Hz, and 90 Hz.

i. FIG. 22 illustrates a comparison of time course of twitch tension in control vs. LASSBio-294.

j. FIG. 23 is a graphic representation of the relationship between fractional twitch tension and LASSBio-294 concentration from 0 to 100 µm.

k. FIG. 24 shows time parameters measured during twitch tension time course. Table 5 gives the time parameters experimentally measured in vehicle control and LASSBio-294 12.5 µM.

l. FIG. 25 is a graphic representation of effect of LASSBio-294 on time course of fatigue development, comparing Ringer's solution, vehicle control and LASSBio-294 12.5 µM.

m. FIG. 26 shows data giving the time course of the index of fatigue development.

n. FIG. 27 is a graphic representation of the time for tetanic force to decrease to 50% of original tetanic force comparing Ringer's solution to 12.5, 25, and 50 µM of LASSBio-294.

o. FIG. 28 is a graphic representation of the time required tetanic force to decrease (fatigue) to 50% of the pre-fatigue tetanic force.

p. FIG. 29 is a graphic representation of the time to recovery to 80% of the pre-fatigue tetanic force.

General Method:

The tests in amphibians were performed in isolated single muscle cells freshly isolated from either the semitendinous or the tibialis anterior muscles of the frog, rana pipiens. The isolated muscle cells were left resting for at least half an hour in Ringer's solution. The fibers were then stimulated with single, low-voltage, electric shocks. If fibers gave brisk twitches and had no signs of membrane damage, they were used. Otherwise, they were discarded. Healthy fibers were transferred to the experimental chamber, which consisted of a 0.3 ml narrow channel where the solutions could be changed several times within five seconds. One tendon of the fiber was gripped with a small clamp and the other tendon was attached to a hook of an Ekhart;s type force transducer. The stimulating electrode consisted of platinum wires placed to each side of the fiber. The muscle fibers were stretched 1.3 times their slack length to reach approximately an average sarcomere length of 1.6 µm.

The fibers were stimulated with single electric pulses of 0.5 msec duration and variable voltage. The voltage was increased until the threshold for contraction was reached. This voltage was then increased by 50% and the experimental protocol started. To find out if LASSBio-294 has an effect on contractility, a stimulating protocol was used consisting of a series of single twitches elicited every 3 sec. followed by different frequencies of tetanic stimulation of 10 Hz, 30 Hz, and 60 Hz. The fibers rested for three minutes between each tetanic stimulation. When the whole series of stimulations were repeated, the fibers rested for 10 min. between each series of twitches and tetanic stimulations. Fatigue was induced by repetitive cycles of electrical stimulation. Each cycle consisted of a train of electric shocks delivered at 60 Hz for 0.8 sec followed by a single twitch after 2.2 sec and repeated every 4.15 sec. To compare different curves of fatigue development from different preparations, we have used a fatigue index at different times of stimulation by taking the ratio of maximum tetanic tension produced during every 3rd tetanus to the tension output in the 1st tetanus i.e. $T_n/T_1$.

The first series of tests were done with LASSBio-294 in normal Ringer and then in Ringer's solution plus LASSBio-294.

Solutions:

The Ringer's solution contained, in mM: NaCl, 115; KCl, 2.5; $CaCl_2$, 1.8; $MgCl_2$, 0.2. pH was adjusted with phosphates to 7.2.

A stock solution of 50 mM LASSBio-294 was dissolved in Ringer's solution to produce a 100 µM solution by diluting 40 µl of the original 50 mM LASSBio-294 in 20 ml of Ringer's solution. From this 100 µM 294 compound solution final dilutions were prepared; e.g. for a 12.5 µM LASSBio-294 solution, 1.25 ml of the 100 µM solution was dissolved in 10 ml of normal Ringer's solution.

Single twitches. As shown in FIGS. 15 and 16, three minutes after the fiber was bathed with 12.5 µM of LASSBio-294, twitch peak tension increased by approximately 25% when compared with control values. However, when a second cycle of different frequencies of stimulation was repeated 17 min. after the fiber had been in LASSBio-294, twitch tension had increased by approximated 50% of the control value. Washing away LASSBio-294 with normal Ringer induced five min later a further twitch potentiation (FIG. 16). During the second stimulating cycle and 17 min. after the fiber was in Ringer without LASSBio-294, twitch tension was further potentated by approximately 77% of the control value. Afterwards, the fiber was exposed again to 12.5 µM of LASSBio-294. This caused a decrease in twitch force. However, twitch tension was still potentated above the control valve.

Example 8

Figure 30:
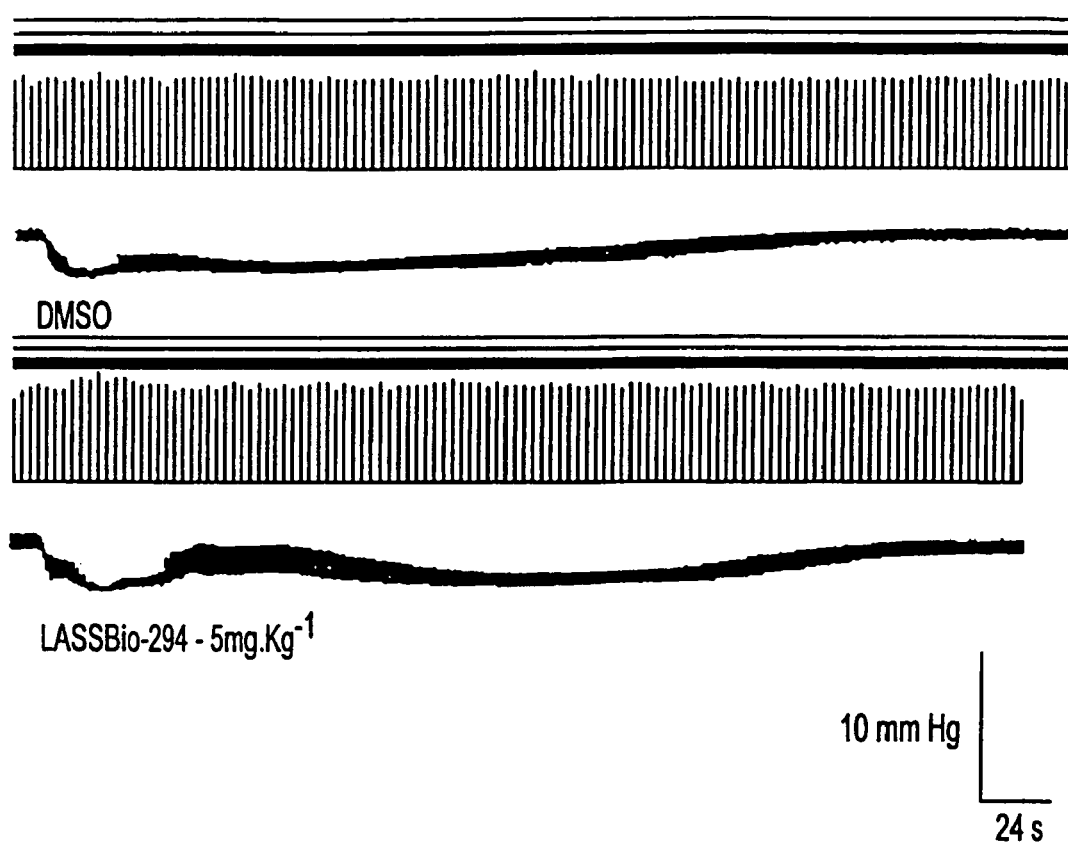
FIG. 30. Records of contractions induced by stimulation of the sciatic nerve of equilibrated rat gastrocnemius muscles and of arterial pressure. In control, contractions were induced by intravenous injection of DMSO (–175 ml). LASSBio-294 was administered in DMSO. Calibration: Horizontal, 1 cm=24 s; Vertical 2 g=100 mm Hg.

Isolated Skeletal Muscle a. FIG. 30 illustrates a test to measure muscle tension stimulation, comparing LASSBio-294 treated with vehicle control. LASSBio-294 has no effect on the neuromuscular junction.

b. FIG. 31 illustrates a test to measure muscle tension after neural stimulation, comparing LASSBio-294 to vehicle control. LASSBio-294 has no effect on neuromuscular transmission.

General Method

Small bundles of fibers were dissected from the extensor digitorum longus (EDL) or the soleus (SOL) muscles of young and adult rats. Rats were anesthetized with ether, and the EDL or SOL muscles were removed quickly and placed in a bicarbonate buffer: Krebs' solution of the following composition in mM: NaCl, 118 µM; KCl, 4.7 µM; $KH_2 PO_4$, 1.2 µM; $MgCl_2$, 0.6 µM; $NaHCO_3$, 25 µM; glucose, 11 µM, and $CaCl_2$, 2.5; equilibrated with 95% $O_2$-5% $CO_2$ to a pH of 7.4 at 22° C. Bundles of 100 to 150 fibers were carefully dissected under a stereo microscope. A new chamber has been designed which allows for bubbling the solution with the $O_2$, CO2 gas mixture directly in the chamber instead of in a separate container. This avoids a continuous flow of bathing solution that would cause the use of a very large amount of LASSBio-294. Prior experimentation had determined the degree of gas flow necessary for the mammalian preparations to survive in a healthy state during a long period of time.

Example 9

Kinetics

Measurement of plasma concentrations of LASBio-294 revealed a retention time (RT) of 14.59 minutes. The plasma concentration of the drug reached a maximum at that time and afterwards tapered off to control levels within 2 hours.

Effects on ATPases

The compound did not affect either $Ca^{2+}$-ATPase or $Na^+/K^+$-ATPase extracted from heart muscle or gastrocnemius muscle of the rat, as well as binding was not affected by the compounds. Determination of phosphodiesterase direct effect was also negative.

Example 10

Studies of LASSBio-294 using the rat thoracic aorta.

Introduction

In vascular smooth muscle, an increase in the content of the second messenger cyclic GNP causes vasodilatation, either by reducing the cytoplasmic $Ca^{2+}$ and/or $Ca^{2+}$ sensitivity of the contractile machinery. Cyclic GMP, as well as cyclic AMP, are degraded by phosphodiesterase isoenzymes (PDE), which have been classified into at least seven isoenzymes families, according to the nucleotide preferentially hydrolyzed and to the regulatory properties of the enzyme: PDE 1 ($Ca^{2+}$-calmodulin dependent), PDE 2 (cyclic GMP-stimulated), PDE 3 (cyclic GNP-inhibited), PDE 4 (cyclic AMP-specific PDE) and PDE 5 (cyclic GMP-specific PDE). The main objective of the present work was to investigate the vascular actions of the recently synthesized inotropic drug namely LASSBio-294.

Results

Figure 32:
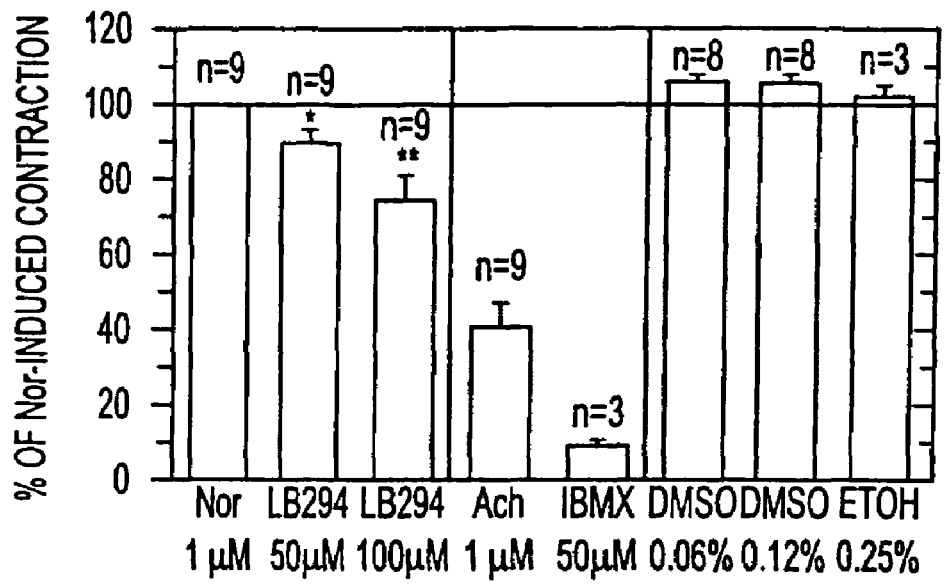
FIG. 32. Effect of LASSBio-294 on 1 µM noradrenaline-indicated rat aorta contraction. The drugs were added after 1 µM Nor maximal effect. *p=0.023 versus control, p=0.000 versus DMSO 0.06%**p=0.001 versus control, p=0.002 versus DMSO 0.12%
Figure 33:
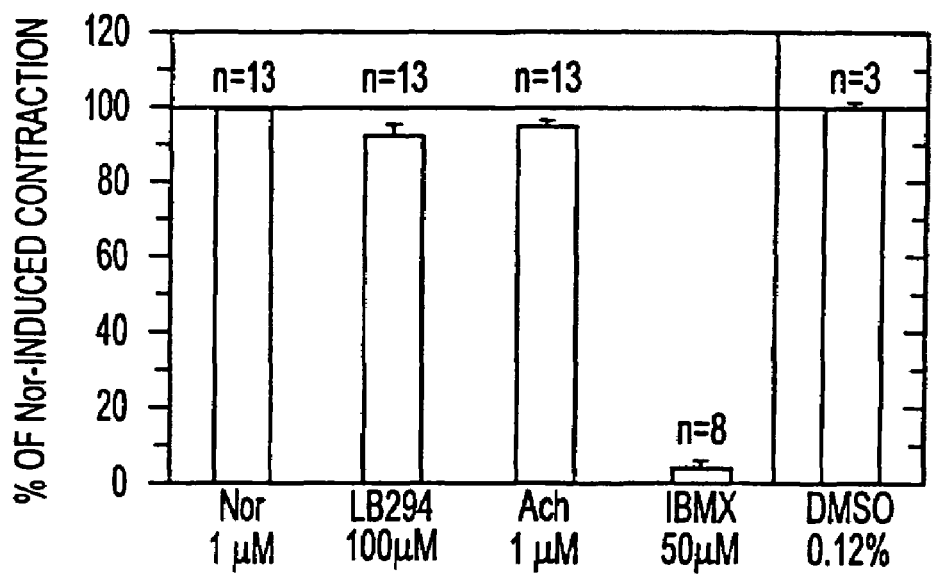
FIG. 33. Effect of LASSBio-294 on endothelium-denuded rat aorta. The drugs were added at 1 µM Nor maximal effect. *p=0.05 versus control FIG. 34. Independence of NO for the LASSBio 294-induced rat aorta relaxation. The drugs were added at 1 µM Nor maximal effect. *p=0.01 versus DMSO 0.12%
Figure 34:
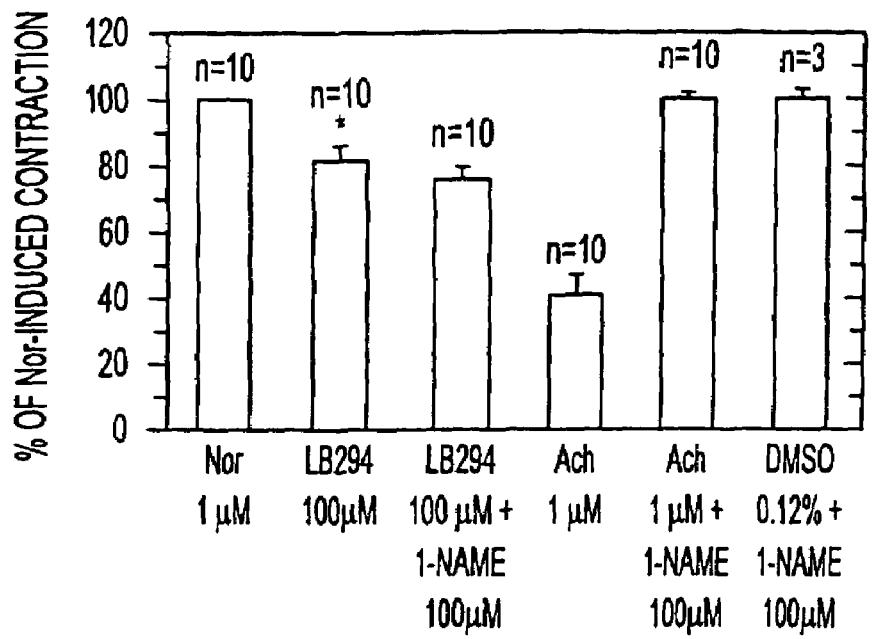
Figure 35:
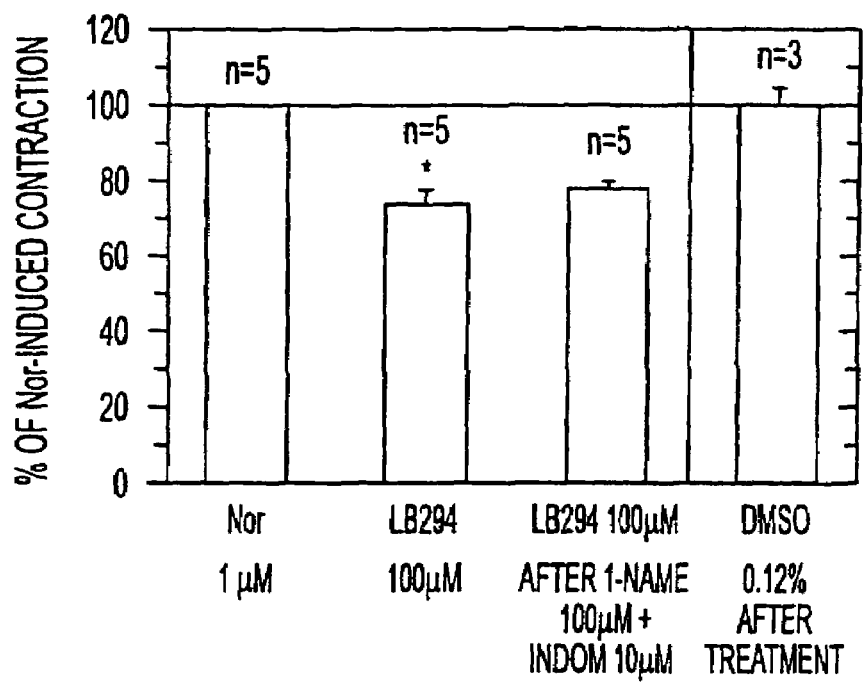
FIG. 35. LASSBio-294 effect on rat aorta pretreated with 1-NAME and indomethacin. The drugs were added at 1 µM Nor maximal effect. *p=0.01 versus DMSO 0.12%
Figure 36:
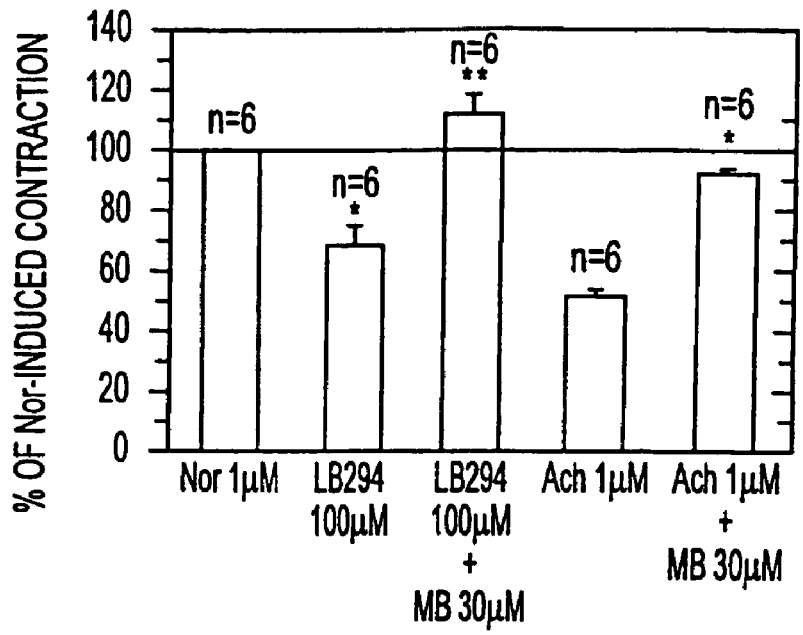
FIG. 36. Reversal of LASSBio 294-induced rat aorta relaxation by 30 µM methylene blue. The drugs were added at 1 µM Nor maximal effect. *, #p=0.001 versus Nor 1 µM and Ach 1 µM, respectively. **p=0.002 versusLB294 100 µM.
Figure 37:
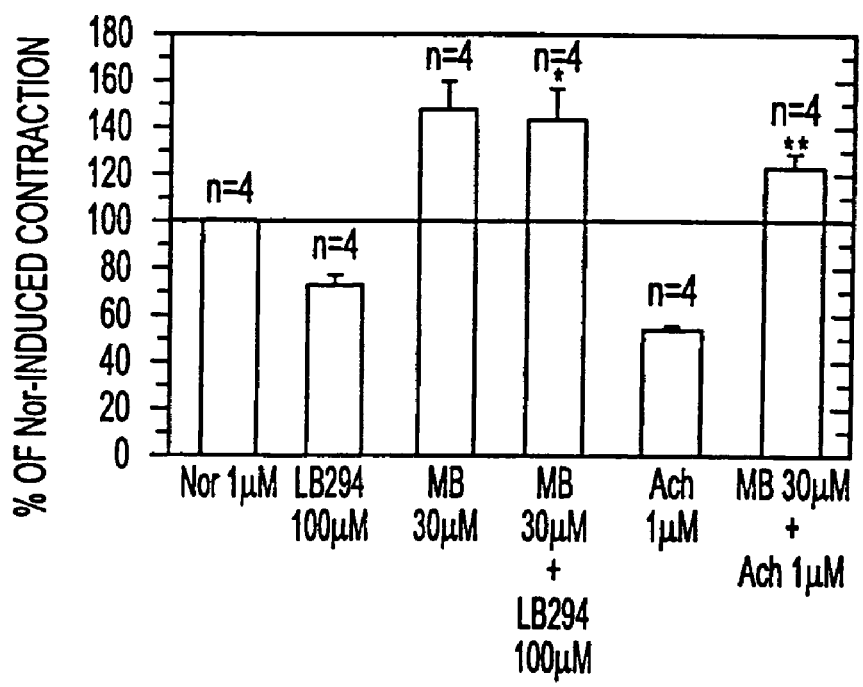
FIG. 37. Pre-treatment with 30 µM methylene blue abolishes LASSBio-294-induced rat aorta relaxation. The drugs were added at 1 µM, the Nor maximal effect. *, ** p=0.000 versus LB294 100 µM and Ach 1 µM, respectively.

LASSBio-294 100 µM relaxed noradrenaline-precontracted aortic rings (FIG. 32), although more slowly than the acetylcholine- and IBMX-induced relaxation. However, in endothelium-denuded aorta this relaxation was abolished, indicating an endothelial contribution to its effect (FIG. 33). In order to establish a possible involvement of 1-arginine/nitric oxide (NO) pathway the aortic rings were treated with the nitric oxide synthase (NOS) inhibitor 1-NAME (100 µM) during 30 min. This treatment caused no difference in the relaxation induced by LASSBio-294 (FIG. 34), suggesting no direct role for NO. The pharmacological inhibition of both NOS and cycloxigenase pathways caused the same level of relaxation observed in the presence of only 1-NAME (FIG. 35). Finally, the relaxation induced by LASSBio-294 was reversed by the addition of 30 µM methylene blue, an inhibitor of soluble guanylate cyclase (FIGS. 36, 36A). Furthermore when methylene blue was added before LASSBio-294, the later was not able to induce relaxation (FIG. 37). In preliminary assays ODQ 10 µM also prevented the vasorelaxation induced by LASSBio-294 100 µM.

Discussion

LASSBio-294 relaxed intact aortic rings in a concentration-dependent manner, however its effect was less pronounced than either endothelium dependent and independent relaxation produced by acetylcholine and IBMX (a non-specific phosphodiesterase PDE inhibitor), respectively. Furthermore its effect was abolished by the removal of the endothelial cells. Delpy and Gouville (1996) recently reported that DMPPO, an inhibitor of PDE 5, also lost its effect after the removal of endothelium. As this relaxant effect could be due to the activation of 1-arginine/NO pathway we investigated the influence of the NOS inhibitor on LASSBio-294 effect. 1-NAME treatment caused no difference in the relaxation elicited by LASSBio-294 indicating that basal vascular NO was not directly involved in this response, despite the endothelial dependence for the vaso-relaxant effect. Furthermore when the tissue was treated with 1-NAME plus indomethacin, the relaxant effect induced by LASSBio-294 was the same as observed in the presence of 1-NAME alone, discarding a direct contribution of $PGI_2$. The relaxant effect of LASSBio-294 was fully reversed by the addition of methylene blue, an inhibitor of soluble guanylate cyclase, and prevented by the pretreatment of this tissue with it, which might reflect an increase in the aortic cyclic GMP and/or cyclic AMP content induced by LASSBio-294. In preliminary results ODQ, a selective inhibitor of soluble guanylate cyclase, had the same effect of methylene blue. Delpy and colleagues (1996) showed that in vascular smooth muscle methylene blue also impaired isoprenaline-induced relaxation, due to a cross-talk between these two nucleotides, where cyclic GMP could enhance cyclic AMP mediated vascular relaxation through the inhibition of PDE 3. LASSBio-294 did not inhibit directly particulate PDE 3 and 4 iso-forms present in rabbit and rat heart, respectively. As a conclusion, the inotropic agent LASSBio-294 has vasodilator activity. A non-limiting explanation is that LASSBio 294 works by increasing cyclic GNP and/or cyclic AMP.

General Method

Aortic rings: Male wistar rats (300–350 g) were anaesthetized with ether and killed by cervical dislocation. The thoracic aorta was quickly removed, placed in physiological solution, cleaned of fat and connective tissue, and cut into 3-mm rings. In some experiments endothelium was mechanically removed by gently rubbing inverted rings on a cotton surface moistened with physiological solution. The rings were fixed in an organ bath chamber filled with physiological solution (composition (mM): NaCl 122, KCl 5, $NaHCO_3$ 15, glucose 11.5, $MgCl_2$ 1.25, $CaCl_2$ 1.25 and $KH_2PO_4$ 1.25) aerated with $O_2/CO_2$, maintained at 37° C., and left to equilibrate for 60 min during which the physiological solution was changed twice. All experiments were carried out under an initial tension of 20 mN, and the developed active tension was measured isometrically using a Grass Transducer (FT03). Data were acquired and analyzed by Chart 3.4/s software (MacLab, USA). The contraction was induced by 1 µM Noradrenaline (NOR) and when it reached a plateau the relaxant drugs (or solvent—time-matched control) were added. The rings contracted with 1 µM NOR that relaxed 40–50% in response to 1 µM acetylcholine were considered with intact endothelium.

Drugs: LASSBio-294 and ODQ were dissolved in 100% dimethyl sulphoxide (DMSO). Noradrenalin, 1-NAME, IBMX, methylene blue, acetylcholine and indomethacin were purchased from SIGMA (USA). All drugs but indomethacin were dissolved in water in the day of the experiment. Indomethacin was dissolved in 5% sodium carbonate. Statistics: Data are presented as mean ±sem. Statistical analysis was performed using the Primer software. Vasodilator responses are expressed in percentage of the maximal contraction induced by 1 µM NOR. Differences were considered significant at p<0.05 (Student's t test).

Example 11

Composition of a Tablet

| | |
|---|---|
| 0.01 mg | LASSBio |
| 90 mg | Lactose anhydrate |
| 9.45 mg | Glycerol behenate |
| 0.5 mg | Magnesium stearate |

Example 12

Composition of a Parentarel

| | |
|---|---|
| 0.01 mg | LASSBio 294 |
| 100 mg | Polysorbate 90 |
| 900 mg | water |

Example 13

Composition of an Injectable

| | |
|---|---|
| 1 mg | LASSBio |
| 150 mg | soybean oil |
| 50 mg | diacetylated monoglyceride |
| 50 mg | water |
| | sodium hydroxide to adjust pH |

Example 14

Composition of a Tablet

| | |
|---|---|
| 0.01 mg | LASSBio |
| 10 mg | magnesium stearate |
| 90 mg | microcrystaline cellulose |

Example 15

Composition of a Sublingual Solution

| | |
|---|---|
| 1 mg | LASSBio |
| 25 mg | Tween 20 |
| 60 mg | Linoleic Acid |
| 10 mg | water |

Example 16

Composition of a Suppository

| | |
|---|---|
| 0.1 mg | LASSBio |
| 50 mg | glycerin |
| 150 mg | glyceryl mono stearate |
| 700 mg | hydrogenated coconut oil |
| 100 mg | hydrogenated fatty acids |

Example 17

Composition of a Liquid

| | |
|---|---|
| 10 mg | Tween 20 |
| 10 mg | glycerin |
| 10 mg | propylene glycol |
| 0.1 mg | sodium benzoate |
| 0.1 mg | citric acid |
| 50 mg | sucrose |
| 800 mg | water |

What is claimed is:

1. A chemical compound having the formula (I)

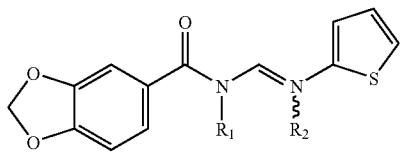

wherein,

R$_1$ is selected from the group consisting of hydrogen, allyl of 1 to 6 carbon atoms, unsubstituted phenyl, and substituted phenyl;

R$_2$ is selected from the group consisting of H, alkene, un-substituted phenyl, and substituted phenyl; or a pharmaceutically acceptable salt thereof.

2. The chemical compound according to claim 1, wherein at least one of R$_1$ and R$_2$ is hydrogen.

3. The chemical compound according to claim 1, wherein R$_1$ is hydrogen.

4. The chemical compound according to claim 1, wherein R$_2$ is hydrogen.

5. The chemical compound of claim 1, wherein R$_1$ is hydrogen;

and R$_2$ is hydrogen; and pharmaceutically acceptable salts thereof.

6. A method of preparing the chemical compound according to claim 5, comprising:
contacting 3,4-methylenedioxybenzoylhydrazine with an equimolar amount of thiophene-2-carboxaldehyde; and recovering the compound.

7. The method according to claim 6, wherein said thiophene-2-carboxaldehyde is in a solvent and in the presence of a catalyst.

8. The method according to claim 7, wherein said solvent is ethanol and said catalyst is hydrochloric acid.

9. A pharmaceutical composition comprising the compound of claim 5 in combination with a pharmaceutically acceptable carrier.

10. The pharmaceutical composition of claim 9, further comprising pharmaceutically acceptable inactive ingredient selected from diluents, solvents, disintregrants, lubricants, stabilizers, or coatings.

11. The pharmaceutical composition of claim 10, wherein the composition is formulated for oral administration.

12. The pharmaceutical composition of claim 9, wherein the composition is formulated for parentral administration.

13. A pharmaceutical composition, comprising the compound of claim 1 in combination with a pharmaceutically acceptable carrier.

14. A pharmaceutical composition, comprising the compound of claim 2 in combination with a pharmaceutically acceptable carrier.

15. A pharmaceutical composition, comprising the compound of claim 3 in combination with a pharmaceutically acceptable carrier.

16. A pharmaceutical composition, comprising the compound of claim 4 in combination with a pharmaceutically acceptable carrier.

17. A method of treating congestive heart failure in a patient, comprising administering a therapeutically effective amount of the compound of claim 5.

18. The method of treating a patient according to claim 17, wherein the therapeutically effective amount of the compound is one that produces a plasma concentration of the compound of 1 µM to 100 µM.

19. The method of treating a patient according to claim 18, wherein the therapeutically effective amount is one that produces a plasma concentration of the compound of 10 µM to 50 µM.

20. A method of treating congestive heart failure in a patient, comprising administering a therapeutically effective amount of the compound of claim 3.

21. A method of treating congestive heart failure in a patient, comprising administering a therapeutically effective amount of the compound of claim 4.

* * * * *